United States Patent
Imura et al.

(10) Patent No.: US 10,662,300 B2
(45) Date of Patent: May 26, 2020

(54) METHOD FOR PRODUCING POLYACRYLIC ACID (SALT)-BASED WATER-ABSORBENT RESIN

(71) Applicant: Nippon Shokubai Co., Ltd., Osaka (JP)

(72) Inventors: Motohiro Imura, Himeji (JP); Hidenori Wada, Himeji (JP); Seiji Kato, Himeji (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 0 days.

(21) Appl. No.: 14/888,964

(22) PCT Filed: May 9, 2014

(86) PCT No.: PCT/JP2014/062448
§ 371 (c)(1),
(2) Date: Nov. 4, 2015

(87) PCT Pub. No.: WO2014/181859
PCT Pub. Date: Nov. 13, 2014

(65) Prior Publication Data
US 2016/0083533 A1 Mar. 24, 2016

(30) Foreign Application Priority Data

May 10, 2013 (JP) ................... 2013-099764

(51) Int. Cl.
*C08J 3/24* (2006.01)
*A61L 15/24* (2006.01)

(52) U.S. Cl.
CPC .............. *C08J 3/245* (2013.01); *A61L 15/24* (2013.01); *C08J 2333/02* (2013.01); *C08J 2333/08* (2013.01)

(58) Field of Classification Search
CPC ......... C08J 3/245; C08J 2333/02; C08F 22/02
USPC ...................................................... 525/329.7
See application file for complete search history.

(56) References Cited

U.S. PATENT DOCUMENTS

| | | | |
|---|---|---|---|
| 5,096,944 | A | 3/1992 | Itou et al. |
| 5,672,633 | A | 9/1997 | Brehm et al. |
| 6,323,252 | B1 | 11/2001 | Gartner et al. |
| 6,414,214 | B1 | 7/2002 | Engelhardt et al. |
| 6,720,389 | B2 | 4/2004 | Hatsuda et al. |
| 7,378,453 | B2 | 5/2008 | Nogi et al. |
| 7,507,475 | B2 | 3/2009 | Inger et al. |
| 2002/0061978 | A1 | 5/2002 | Hatsuda et al. |
| 2004/0186244 | A1 | 9/2004 | Hatsuda et al. |
| 2009/0186542 | A1 | 7/2009 | Kondo et al. |
| 2010/0323885 | A1 | 12/2010 | Herfert et al. |
| 2011/0028670 | A1 | 2/2011 | Matsumoto et al. |
| 2011/0040044 | A1 | 2/2011 | Motoyama et al. |
| 2011/0166300 | A1 | 7/2011 | Dairoku et al. |
| 2011/0319518 | A1 | 12/2011 | Kadonaga et al. |
| 2012/0172536 | A1 | 7/2012 | Nogi et al. |
| 2014/0193641 | A1* | 7/2014 | Torii ................. C08F 20/06 428/402 |
| 2015/0210843 | A1* | 7/2015 | Kimura ................ A61L 15/60 525/187 |

FOREIGN PATENT DOCUMENTS

| | | | |
|---|---|---|---|
| CN | 101981090 | A | 2/2011 |
| CN | 102124039 | A | 7/2011 |
| EP | 2896454 | A1 | 7/2015 |
| JP | 01-113406 | * | 5/1989 |
| JP | 01297430 | | 11/1989 |
| JP | 09-124879 | | 5/1997 |
| JP | 3195705 | B2 | 8/2001 |
| JP | 2002201290 | A | 7/2002 |
| JP | 201212482 | | 1/2012 |
| JP | 2016-113465 | A | 6/2016 |
| WO | WO-2009125849 | A1 | 10/2009 |
| WO | WO-2012133734 | A1 | 10/2012 |
| WO | WO 2013/002387 | A1 * | 1/2013 |
| WO | WO 2014/041969 | A1 * | 3/2014 |
| WO | WO-2014162843 | A1 | 10/2014 |

OTHER PUBLICATIONS

Dewpoint Calculator; http://www.decatur.de/javascript/dew/; 2016.*
JP 01-113406, machine translation; 1989.*
International Preliminary Report on Patentability dated Nov. 10, 2015.
International Search Report dated Aug. 19, 2014.
Chinese Office Action and English translation thereof dated Nov. 1, 2016.

(Continued)

*Primary Examiner* — Hui H Chin
(74) *Attorney, Agent, or Firm* — Harness Dickey & Pierce P.L.C.

(57) ABSTRACT

A method is disclosed for inexpensively and stably producing, with high productivity, water absorbent resin having excellent damage resistance. A method for producing a polyacrylic acid (salt)-based water absorbent resin, the method comprising a surface-crosslinking step, the surface-crosslinking step including a reaction step, the reaction step involving using a reactor having (i) an inner wall surface having a temperature within a range of 100° C. to 250° C. and (ii) an inside atmosphere having a dew point within a range of 60° C. to 100° C., the reaction step including heat-treating a water absorbent resin mixture so as to produce water absorbent resin powder having a temperature within a range of 90° C. to 130° C.

14 Claims, No Drawings

(56) References Cited

OTHER PUBLICATIONS

Database WPI Week 201469, Thompson Scientific, London, GB; AN 2014-S17630.
European Search Report dated Aug. 11, 2016 in European patent application No. 14795139.6.

\* cited by examiner

METHOD FOR PRODUCING POLYACRYLIC ACID (SALT)-BASED WATER-ABSORBENT RESIN

TECHNICAL FIELD

The present invention relates to a method for producing a polyacrylic acid (salt)-based water absorbent resin. More particularly, the present invention relates to a method for producing a polyacrylic acid (salt)-based water absorbent resin which method includes controlling a reaction condition for a surface-crosslinking treatment to stably and continuously produce water absorbent resin having excellent damage resistance and high performance.

BACKGROUND ART

Water absorbent resin (super absorbent polymer [SAP]) is a water-swellable, water-insoluble polymer gelatinizer. Water absorbent resin is capable of absorbing a water-based liquid in such a large amount as corresponding to several times to several hundreds of times the self weight. Water absorbent resin thus finds a wide range of applications, including (i) sanitary products such as disposable diapers, sanitary napkins, and incontinence pads, (ii) agricultural and horticultural water retaining agents, (iii) industrial water-proofing agents, and the like.

For such water absorbent resin, there have been proposed many monomers and hydrophilic polymers as raw materials. Industrially most common among different water absorbent resins is a polyacrylic acid (salt)-based water absorbent resin containing acrylic acid and/or a salt thereof as a monomer for high water absorbing ability.

The water absorbent resin is required to have various functions (excellent physical properties), as disposable diapers, which is a main application of the water absorbent resin, have increasingly higher performance. Specifically, the water absorbent resin is required to have, in addition to basic physical properties such as water absorption capacity without load and water absorption capacity under load, improved physical properties such as gel strength, water-soluble component, moisture content, water absorbing speed, liquid permeability, particle size distribution, urine resistance, antibacterial property, damage resistance, powder fluidity, deodorant property, anti-coloring property, low dustiness, and low monomer residual. There have been proposed various techniques for improving the above physical properties. Specifically, Patent Literatures 1 to 13 listed below each disclose a technique such as changing surface crosslinking, additive, or production process.

The techniques proposed include, in particular, techniques of surface-crosslinking water absorbent resin such as a technique of controlling a relative humidity and/or dew point of an atmosphere during a heat treatment to adjust the moisture in water absorbent resin (Patent Literatures 1 and 2), a technique in which a device for cooling water absorbent resin after a heat treatment has a defined size (Patent Literature 3), a technique of adding a water-based liquid to water absorbent resin during a heat treatment (Patent Literature 4), and a technique of carrying out a surface-crosslinking reaction twice (Patent Literature 5).

The techniques proposed further include methods for modification after surface crosslinking such as a technique of adding water to surface-crosslinked water absorbent resin for granulation (Patent Literature 6), a technique of adding a water-based liquid to heat-treated water absorbent resin when cooling the water absorbent resin for granulation (Patent Literature 7), a technique of adding a water-based liquid to heat-treated water absorbent resin for improved damage resistance (Patent Literature 8), a technique of adjusting the moisture content of a product for improved damage resistance (Patent Literature 9), a technique of humidifying and mixing water absorbent resin again after a heat treatment to increase the moisture content of the water absorbent resin (Patent Literature 10), a technique of adding a polyhydric metal salt aqueous solution to surface-crosslinked water absorbent resin (Patent Literatures 11 and 12), and a technique of adding an alkanolamine aqueous solution to surface-crosslinked water absorbent resin (Patent Literature 13).

Water absorbent resin produced with use of a technique mentioned above such as a surface-crosslinking technique, however, may be subjected to a mechanical damage during a step such as a conveying step or a filling step or even while a user, for example, processes the water absorbent resin into an absorbent article such as a disposable diaper. Such a mechanical damage, for example, destroys a surface-crosslinked layer of the water absorbent resin or even particles thereof, which has led to generation of dust or degradation of the physical properties.

The above phenomenon is a problem related to damage resistance of water absorbent resin. To solve this problem, there has been proposed a technique of adding water or an aqueous solution to surface-crosslinked water absorbent resin (Patent Literatures 9 to 13).

CITATION LIST

Patent Literature 1
Japanese Patent Publication No. 2020021
Patent Literature 2
U.S. Pat. No. 6,720,389, specification
Patent Literature 3
U.S. Patent Application No. 2012/0172536, specification
Patent Literature 4
Japanese Patent Application Publication, Tokukaihei, No. 3-195705 A (1991)
Patent Literature 5
U.S. Pat. No. 5,672,633, specification
Patent Literature 6
U.S. Pat. No. 5,096,944, specification
Patent Literature 7
U.S. Pat. No. 7,378,453, specification
Patent Literature 8
Japanese Patent Application Publication, Tokukaihei, No. 9-124879 A (1997)
Patent Literature 9
U.S. Patent Application No. 2009/0186542, specification
Patent Literature 10
U.S. Patent Application No. 2010/0323885, specification
Patent Literature 11
U.S. Pat. No. 7,507,475, specification
Patent Literature 12
U.S. Pat. No. 6,323,252, specification
Patent Literature 13
U.S. Pat. No. 6,414,214, specification

SUMMARY OF INVENTION

Technical Problem

As described above, there have been proposed many surface-crosslinking techniques and the like to improve the physical properties of water absorbent resin. Those techniques include, in particular, a method for surface-crosslinking water absorbent resin (Patent Literatures 1 to 5) and a method for increasing the moisture content of surface-crosslinked water absorbent resin (Patent Literatures 8 to 13) to produce water absorbent resin that generates a reduced amount of fine powder and that has excellent damage resistance, as disposable diapers have increasingly higher performance.

The techniques disclosed in Patent Literatures 1 to 7 above, however, leave water absorbent resin adhering to, for example, an inner wall of a mixing apparatus, a reactor, or a cooling apparatus during production of water absorbent resin having damage resistance and a high moisture content. This has prevented a stable, continuous production, and has possibly decreased productivity or degraded the physical properties.

The techniques disclosed in Patent Literatures 8 to 13 above, for improved damage resistance (impact resistance), use as a water-based liquid an aqueous solution in which an inorganic compound, polyhydric metal salt, or alkanolamine is dissolved. This has contrarily required a cost increase for a reduction of the amount of fine powder generated of water absorbent resin and for an improvement in the damage resistance of water absorbent resin.

It is therefore an object of the present invention to provide a method for inexpensively and stably producing, with high productivity, water absorbent resin having excellent damage resistance.

Solution to Problem

In order to solve the above problem, the inventors of the present invention have diligently studied a method for producing water absorbent resin, in particular different conditions for a surface-crosslinking step, to finally obtain the knowledge below and complete the present invention.

Specifically, the inventors of the present invention have discovered that (i) such physical properties of water absorbent resin as damage resistance, high moisture content, and water absorption capacity under load depend on the dew point of the atmosphere in a heating device used during the surface-crosslinking step (reaction step) and the temperature of water absorbent resin in the heating device and that (ii) whether it is possible to prevent adherence of water absorbent resin to the heating device or the like is influenced by the temperature of the atmosphere in the heating device and the temperature of the inner wall surface of the heating device.

The discovery indicates that in order to improve the physical properties of water absorbent resin or stably produce water absorbent resin, it is important to control the production process to satisfy all the above conditions (namely, the dew point of the atmosphere in the heating device, the temperature of the atmosphere in the heating device, the temperature of the inner wall surface of the heating device, and the temperature of the water absorbent resin).

The present invention, therefore, provides a method for producing a polyacrylic acid (salt)-based water absorbent resin, the method including a surface-crosslinking step, the surface-crosslinking step including a reaction step, the reaction step involving using a reactor having (i) an inner wall surface having a temperature within a range of 100° C. to 250° C. and (ii) an inside atmosphere having a dew point within a range of 60° C. to 100° C., the reaction step including heat-treating a water absorbent resin mixture to control a powder temperature so that the powder temperature is 90° C. to 130° C.

Advantageous Effects of Invention

The method of the present invention makes it possible to, even without an additional step of increasing the moisture content after the surface-crosslinking step, stably produce water absorbent resin that has an excellent water absorption capacity under load, excellent damage resistance, and a high moisture content.

DESCRIPTION OF EMBODIMENTS

The following description will discuss in detail a method of the present invention for producing a polyacrylic acid (salt)-based water absorbent resin. The scope of the present invention is, however, not limited to this description. Besides the examples below, the present invention can also be (i) modified as appropriate so as not to fail to attain the object of the present invention and (ii) put into practice. Specifically, the present invention is not limited to the description of the embodiments below, and can therefore be modified by a skilled person in the art within the scope of the claims. Any embodiment derived from a proper combination of technical means disclosed in different embodiments is also encompassed in the technical scope of the present invention.

[1] Definitions of Terms (1-1) "Water Absorbent Resin"

The term "water absorbent resin" for the present invention refers to a water-swellable, water-insoluble polymer gelatinizer having, as physical properties, (i) water swellability represented by a CRC (water absorption capacity without load) of not less than 5 (g/g) and (ii) water insolubility represented by an Ext (water-soluble component) of not more than 50 weight %.

The water absorbent resin can be designed as appropriate in correspondence with the application and/or purpose, and is not limited to any particular structure. The water absorbent resin is, however, preferably a hydrophilic crosslinked polymer produced by crosslinking and polymerizing an unsaturated monomer containing a carboxyl group.

The water absorbent resin is not limited to a form in which the water absorbent resin is a polymer in its entirety (100 weight %), and may be a water absorbent resin composition containing an additive and/or the like as long as the water absorbent resin composition has the above physical properties (CRC and Ext). The present specification, unless otherwise noted, uses the term "water absorbent resin" to collectively refer to (i) a water absorbent resin composition containing an additive and/or the like, (ii) an intermediate produced during an intermediate step (for example, a mixture produced during a mixing step or a reactant produced during a reaction step), and (iii) a finished product.

In a case where the water absorbent resin is a water absorbent resin composition, the water absorbent resin (polyacrylic acid (salt)-based water absorbent resin) is contained in an amount of preferably 70 to 99.9 weight %, more preferably 75 weight % to 99 weight %, still more preferably 80 weight % to 97 weight %, particularly preferably 80 weight % to 95 weight %, based on the total amount of the water absorbent resin composition.

The water absorbent resin composition preferably contains water as a component other than the water absorbent resin, and further contains a below-described additive as necessary for an increased water absorbing speed and impact resistance.

(1-2) "Polyacrylic Acid (Salt)"

The term "polyacrylic acid (salt)" for the present invention refers to a polymer that contains, as a main component, a repeating unit of acrylic acid and/or a salt thereof (hereinafter referred to as "acrylic acid (salt)") and that optionally contains a graft component.

The expression "main component" means that the acrylic acid (salt) is contained (used) in an amount of typically 50 to 100 mol %, preferably 70 to 100 mol %, more preferably 90 to 100 mol %, still more preferably substantially 100 mol %, based on the total amount of the monomers to be polymerized (excluding a crosslinking agent).

The polyacrylic acid salt, in a case where it is a polymer, essentially contains a water-soluble salt, preferably a monovalent salt, more preferably an alkali metal salt or ammonium salt, still more preferably an alkali metal salt, particularly preferably a sodium salt.

(1-3) "EDANA" and "ERT"

The term "EDANA" is an abbreviation for the European Disposables and Nonwovens Associations. The term "ERT" is an abbreviation for EDANA Recommended Test Methods, which are European standard (de facto international standard) methods for measuring physical properties of water absorbent resin.

For the present invention, physical properties of water absorbent resin are measured in conformity with the ERT master copy (revised in 2002; publicly known literature) unless otherwise specified.

(1-3-1) "CRC" (ERT 441.2-02)

The term "CRC" is an abbreviation for "centrifuge retention capacity", and refers to a water absorption capacity without load (hereinafter referred to also as "water absorption capacity").

Specifically, the CRC refers to a water absorption capacity (unit: g/g) measured after 0.2 g of water absorbent resin in a nonwoven fabric has been freely swollen in a large excess of a 0.9 weight % sodium chloride aqueous solution for 30 minutes and then drained in a centrifuge (250 G).

(1-3-2) "AAP" (ERT 442.2-02)

The term "AAP" is an abbreviation for "absorption against pressure", and refers to a water absorption capacity under load.

Specifically, the AAP refers to a water absorption capacity (unit: g/g) measured after 0.9 g of water absorbent resin has been swollen in a large excess of a 0.9 weight % sodium chloride aqueous solution for 1 hour under a load of 2.06 kPa (0.3 psi).

(1-3-3) "Ext" (ERT 470.2-02)

The term "Ext" is an abbreviation for "extractables", and refers to a water-soluble component.

Specifically, the Ext refers to a value (unit: weight %) obtained by (i) adding 1.0 g of water absorbent resin to 200 ml of a 0.9 weight % sodium chloride aqueous solution, (ii) stirring the mixture at 500 rpm for 16 hours, and (iii) measuring the amount of dissolved polymer through pH titration.

(1-3-4) "Moisture Content" (ERT 430.2-02)

The term "moisture content" refers to a moisture content of water absorbent resin.

Specifically, the moisture content refers to a value (unit: weight %) calculated from a drying loss for a case in which 4.0 g of water absorbent resin has been dried at 105° C. for 3 hours. For the present invention, the amount of water absorbent resin was changed to 1.0 g, and the drying temperature was changed to 180° C. for the measurements.

(1-3-5) "PSD" (ERT 420.2-02)

The term "PSD" is an abbreviation for "particle size distribution", and refers to a particle size distribution measured through sieve classification. A weight average particle diameter (D50) and a particle diameter distribution range are each measured through a method similar to a method disclosed under "(1) Average Particle Diameter and Distribution of Particle Diameter" of European Patent No. 0349240 or PCT International Publication No. 2004/069915.

(1-3-6) Other Physical Properties Defined Through EDANA Methods

The term "pH" (ERT 400.2-02) refers to the pH of water absorbent resin.

The term "FSC" (ERT 440.2-02) is an abbreviation for "free swell capacity", and refers to a free swell capacity (unit: g/g) of water absorbent resin.

The term "flow rate" (ERT 450.2-02) refers to a flow rate of water absorbent resin.

The term "density" (ERT 460.2-02) refers to a bulk specific gravity of water absorbent resin.

The term "respirable particles" (ERT 480.2-02) refers to respirable dust of water absorbent resin.

The term "dust" (ERT 490.2-02) refers to dust contained in water absorbent resin.

(1-4) "Dusting Rate"

The term "dusting rate" for the present invention is an index for estimating the amount of fine powder generated during a process of producing or conveying water absorbent resin. Specifically, the dusting rate refers to a rate at which the amount of particles smaller than 150 μm (fine powder) increases through a damage test (that is, the "paint shaker test" defined in the Examples). A smaller value for the dusting rate indicates a smaller amount of fine powder generation, hence excellent impact resistance.

(1-5) "Powder Relative Humidity"

The term "powder relative humidity" for the present invention is a value calculated through the equation below as an index for controlling the moisture content of surface-crosslinked water absorbent resin.

$$\text{Powder relative humidity (\%)} = \frac{\text{(Water vapor pressure of the atmosphere)}}{\text{(Saturated vapor pressure at the temperature of the water absorbent resin (powder temperature))}} \times 100$$

The word "atmosphere" in the above equation refers to a space present above water absorbent resin in the reaction apparatus. The "Water vapor pressure of the atmosphere" and "Saturated vapor pressure at the temperature of the water absorbent resin (powder temperature)" are determined through the Wagner equation below.

$$\text{Water vapor pressure (hPa)} = Pc \times \exp\{(A \cdot x + B \cdot x^{1.5} + C \cdot x^3 + D \cdot x^6)/(1-x)\}$$

In this equation, Pc (critical pressure) is 221200 (hPa), Tc (critical temperature) is 647.3 (K), x is $1-(t+273.15)/Tc$, A is $-7.76451$, B is 1.45838, C is $-2.7758$, and D is $-1.23303$.

It is publicly known that the moisture content of water absorbent resin depends on the dew point (relative humidity) of the atmosphere and that heating water absorbent resin evaporates moisture in the water absorbent resin to thereby decrease its moisture content. There has been, however, no correlation formula that collectively indicates the relationship between (i) the moisture content of water absorbent resin and (ii) the dew point of the atmosphere and the temperature of the water absorbent resin. In view of this, the inventors of the present invention have conducted diligent research, and have discovered as a result that the moisture content of heated water absorbent resin has good correlation with the powder relative humidity.

Specifically, in a case where there is a difference between the temperature of the atmosphere in the reaction apparatus and the temperature of the water absorbent resin, the temperature of gas near a surface of the water absorbent resin of which the moisture is being evaporated or which is absorbing moisture is either closer to the temperature of the water absorbent resin than to the temperature of the atmosphere in the reaction apparatus or substantially equal to the temperature of the water absorbent resin.

Thus, controlling only the dew point (relative humidity) of the atmosphere in the reaction apparatus fails to factor in the temperature of water absorbent resin (powder temperature) and does not necessarily allow production of water absorbent resin having a desired moisture content. Controlling the powder relative humidity has, in contrast, made it possible to stably produce water absorbent resin having a desired moisture content.

(1-6) Other

The present specification assumes the following: (i) Any range "X to Y" means not less than X and not more than Y. (ii) Unless otherwise noted, the weight unit "t (ton)" refers to a metric ton, and "ppm" refers to ppm by weight or ppm by mass. (iii) The terms "weight" and "mass" are synonymous with each other, the terms "parts by weight" and "parts by mass" are synonymous with each other, and the terms "weight %" and "mass %" are synonymous with each other. (iv) The expression " . . . acid (salt)" means " . . . acid and/or a salt thereof", and the expression "(meth)acrylic" means "acrylic and/or methacrylic".

[2] Method for Producing Polyacrylic Acid (Salt)-Based Water Absorbent Resin (2-1) Polymerization Step This step is a step of polymerizing an acrylic acid (salt)-based monomer aqueous solution to produce a hydrogel-like crosslinked polymer (hereinafter referred to as "hydrogel").

(Monomer) (Excluding a Crosslinking Agent)

The polyacrylic acid (salt)-based water absorbent resin produced through a method of the present invention is, for improved water absorbing ability, preferably made of a monomer as a raw material which monomer contains, as a main component, an acrylic acid (salt) in which the acrylic acid is at least partially neutralized.

The partially neutralized acrylic acid salt is not limited to any particular kind. The partially neutralized acrylic acid salt is, for improved water absorbing ability, preferably one or more monovalent salts selected from an alkali metal salt, an ammonium salt, and an amine salt, more preferably alkali metal salt, still more preferably one or more acrylic acid salts selected from a sodium salt, a lithium salt, and a potassium salt, and particularly preferably a sodium salt.

The neutralization may be carried out on the monomer before the polymerization and/or on the hydrogel after the polymerization. The neutralization has a rate of preferably 10 mol % to 100 mol %, more preferably 30 mol % to 95 mol %, still more preferably 50 mol % to 90 mol %, and particularly preferably 60 mol % to 80 mol %.

The monomer (including a crosslinking agent described below) is typically polymerized in the form of an aqueous solution. The aqueous solution has a monomer concentration (referred to also as "solid content") of typically 10 weight % to 90 weight %, preferably 20 weight % to 80 weight %, still more preferably 30 weight % to 70 weight %, particularly preferably 35 weight % to 60 weight %, and most preferably 40 weight % to 55 weight %.

Further, to improve physical properties of water absorbent resin to be produced, the polymerization step may further involve adding an optional component to the acrylic acid (salt)-based monomer aqueous solution or to the water absorbent resin such as the hydrogel after the polymerization, dried polymer, or pulverized polymer. Examples of the optional component include (i) a foaming agent such as a carbonate, an azo compound, and air bubbles, (ii) an additive such as a surfactant and a chelating agent, (iii) starch, and (iv) a water-soluble or water-absorbent resin such as a polyvinyl alcohol and a polyacrylic acid (salt).

The additive is added in an amount of preferably 0 weight % to 5 weight %, and more preferably 0 weight % to 1 weight %, based on the monomer. The water-soluble or water-absorbent resin is added in an amount of preferably 0 weight % to 50 weight %, more preferably 0 weight % to 20 weight %, still more preferably 0 weight % to 10 weight %, and particularly preferably 0 weight % to 3 weight %, based on the monomer.

For the present invention, the monomer, in a case where it contains an acrylic acid (salt) as a main component in an amount within the above range, may further contain a hydrophilic or hydrophobic unsaturated monomer in addition to the acrylic acid (salt).

The hydrophilic or hydrophobic unsaturated monomer is not limited to any particular one. Examples of the hydrophilic or hydrophobic unsaturated monomer include methacrylic acid, maleic acid (anhydride), 2-(meth)acrylamide-2-methyl propanesulfonic acid, (meth)acryloxyalkanesulfonate, N-vinyl-2-pyrrolidone, N-vinyl acetamide, (meth)acrylamide, N-isopropyl (meth)acrylamide, N,N-dimethyl (meth)acrylamide, 2-hydroxyethyl (meth)acrylate, methoxy polyethylene glycol (meth)acrylate, polyethylene glycol (meth)acrylate, stearyl acrylate, and salts thereof etc.

The hydrophilic or hydrophobic unsaturated monomer is, for improved physical properties of water absorbent resin to be produced, contained in an amount within the range of preferably 0 weight % to 50 weight %, and more preferably 0 weight % to 20 weight %, based on the total amount of the monomer.

(Crosslinking Agent (Internal Crosslinking Agent))

The present invention preferably uses a crosslinking agent (internal crosslinking agent) for an improved water absorbent property. The crosslinking agent (internal crosslinking agent) is not limited to any particular kind. Examples of the crosslinking agent include (i) a crosslinking agent polymerizable with an acrylic acid, (ii) a crosslinking agent reactive with a carboxyl group, and (iii) a crosslinking agent polymerizable with an acrylic acid and reactive with a carboxyl group.

Specifically, the polymerizable crosslinking agent may be a compound having at least two polymerizable double bonds in a molecule such as N,N'-methylene bisacrylamide, (poly) ethylene glycol di(meth)acrylate, (polyoxyethylene)trimethylolpropane tri(meth)acrylate, or poly(meth)allyloxy alkane.

The reactive crosslinking agent may be, for example, (i) a polyglycidyl ether such as ethylene glycol diglycidyl ether, (ii) a covalent bonding crosslinking agent containing, for example, a polyhydric alcohol such as propanediol, glycerin, or sorbitol, or (iii) an ionic bonding crosslinking agent containing, for example, a polyhydric metal compound of aluminum or the like.

The present invention, for an improved water absorbent property, preferably uses, among others, a crosslinking agent polymerizable with an acrylic acid, and suitably uses an acrylate-based, allyl-based, or acrylamide-based polymerizable crosslinking agent in particular. The present invention may use either only one of the above internal crosslinking agents or two or more in combination.

The internal crosslinking agent is, for improved physical properties, used in an amount of preferably 0.001 mol % to 5 mol %, more preferably 0.005 mol % to 2 mol %, still more preferably 0.01 mol % to 1 mol %, and particularly preferably 0.03 mol % to 0.5 mol %, based on the total amount of the monomer excluding the crosslinking agent.

(Polymerization Initiator)

The present invention may use a polymerization initiator selected as appropriate according to the form of the polymerization. Examples of the polymerization initiator include a photolytic polymerization initiator, a pyrolytic polymerization initiator, and a redox polymerization initiator. The polymerization initiator is used in an amount of preferably 0.0001 mol % to 1 mol %, and more preferably 0.001 mol % to 0.5 mol %, based on the total amount of the monomer.

Examples of the photolytic polymerization initiator include a benzoin derivative, a benzyl derivative, an acetophenone derivative, a benzophenone derivative, and an azo compound. Examples of the pyrolytic polymerization initiator include (i) a persulfate such as sodium persulfate, potassium persulfate, or ammonium persulfate, (ii) a peroxide such as hydrogen peroxide, t-butyl peroxide, or methyl ethyl ketone peroxide, and (iii) an azo compound such as 2,2'-azobis(2-amidinopropane)dihydrochloride or 2,2'-azobis[2-(2-imidazoline-2-yl)propane]dihydrochloride.

The redox polymerization initiator is, for example, a system that combines, for example, the persulfate or peroxide with a reductive compound such as L-ascorbic acid or sodium bisulfite. The present invention may preferably use a photolytic polymerization initiator and a pyrolytic polymerization initiator in combination.

(Polymerization Method)

The present invention, for improvement of performance and ease of polymerization control, carries out polymerization through spray polymerization, droplet polymerization, aqueous solution polymerization, or reverse phase suspension polymerization, preferably aqueous solution polymerization, still more preferably continuous aqueous solution polymerization. Water absorbent resin produced through aqueous solution polymerization or continuous aqueous solution polymerization has an irregularly pulverized shape, and likely generates fine powder during a subsequent step such as a pulverization step. The present invention, however, adds a water-based liquid to the water absorbent resin during a surface-crosslinking step, with the result of a reduction in the amount of fine powder generated.

Preferable forms of the continuous aqueous solution polymerization include, for example, a continuous kneader polymerization (disclosed in, for example, U.S. Pat. Nos. 6,987,151 and 6,710,141) and a continuous belt polymerization (disclosed in, for example, U.S. Pat. Nos. 4,893,999 and 6,241,928 and U.S. Patent Application No. 2005/215734). Any of these forms of continuous aqueous solution polymerization makes it possible to produce water absorbent resin with high productivity.

Even through polymerization at such a high concentration or a high temperature, the present invention allows production of water absorbent resin containing a monomer with excellent stability and having high whiteness. The present invention thus brings about a more significant effect under such a condition. Examples of such polymerization initiated at a high temperature are disclosed in U.S. Pat. Nos. 6,906,159, 7,091,253 etc. The method of the present invention, however, also allows a monomer before polymerization to have excellent stability, and thus easily allows industrial scale production.

The above forms of polymerization, each of which may be carried out in an air atmosphere, are each preferably carried out in an atmosphere of an inert gas such as nitrogen or argon (for example, with an oxygen concentration of less than 1% by volume) for coloring improvement. Further, the above forms of polymerization are each preferably carried out after oxygen dissolved in the monomer or in a solution containing the monomer has been substituted sufficiently with an inert gas (for example, with less than 1 mg/L of oxygen dissolved).

(2-2) Gel-Crushing Step

This step is a step of gel-crushing a hydrogel, produced through the polymerization step, with use of a gel-crusher such as a kneader, a meat chopper, or a cutter mill to produce a hydrogel in the form of particles (hereinafter referred to as "particulate hydrogel"). In a case where the polymerization step is carried out through kneader polymerization, such a step is equivalent to a combination of the polymerization step and gel crushing step carried out simultaneously. The hydrogel produced through the polymerization step may skip the gel-crushing step to be fed directly to a drying step. The gel-crushing step may be preceded or followed as necessary by a step of maturing the hydrogel (in particular, a step of promoting, for example, polymerization by means of heating, heat retention, or the like).

This step may further involve adding, to the hydrogel produced through the polymerization step, water, a polyhydric alcohol, a mixture liquid of water and a polyhydric alcohol, a polyhydric metal (salt) aqueous solution, a vapor of any of the above, or the like for improvement of gel-crushability and physical properties.

The present invention has a gel crushing time period (that is, a time period from the end of polymerization to the start of drying) that is preferably short for a reduction of a residual monomer, prevention of gel degradation (improvement in urine resistance), and prevention of yellowing. Specifically, the gel crushing time period is preferably not longer than 1 hour, more preferably not longer than 0.5 hour, and still more preferably not longer than 0.1 hour. Further, during the gel crushing time period, the hydrogel has a temperature controlled (retained or heated) so that the temperature is preferably 40° C. to 95° C., more preferably 50° C. to 80° C., and still more preferably 60° C. to 70° C.

The gel-crushed particulate hydrogel described above has a resin solid content of preferably 10 weight % to 90 weight %, more preferably 20 weight % to 80 weight %, still more preferably 30 weight % to 70 weight %, and particularly preferably 35 weight % to 60 weight %. The particulate hydrogel has a weight average particle diameter (D50) (as measured through sieve classification) of preferably 0.2 mm to 10 mm, more preferably 0.3 mm to 5 mm, and still more preferably 0.5 mm to 3 mm. The particulate hydrogel contains particles each having a diameter of 5 mm or greater at a proportion of preferably 0 weight % to 10 weight %, and more preferably 0 weight % to 5 weight %, based on the entire particulate hydrogel. The respective diameters of the hydrogel particles are measured through the wet classification method disclosed in paragraph [0091] of Japanese Patent Application Publication, Tokukai, No. 2000-63527 A.

(2-3) Drying Step

This step is a step of drying the hydrogel and/or particulate hydrogel, produced through the polymerization step and/or gel crushing step, to a desired resin solid content to produce a dried polymer. The resin solid content is a value determined from a drying loss (that is, a weight change caused in a case where 1 g of a sample has been heated at 180° C. for 3 hours). The resin solid content is preferably not less than 80 weight %, more preferably 85 weight % to 99 weight %, still more preferably 90 weight % to 98 weight %, and particularly preferably 92 weight % to 97 weight %.

The present invention may use any drying method that allows the hydrogel and/or particulate hydrogel to be dried to the resin solid content. The drying method may be selected as appropriate from, for example, drying by heating, hot-air drying, drying under reduced pressure, infrared drying, microwave drying, drum dryer drying, azeotropic dehydration drying involving a hydrophobic organic solvent, and high-humidity drying involving a high-temperature water vapor. The drying method is, among others, preferably hot-air drying, more preferably hot-air drying involving a gas having a dew point of 0° C. to 100° C., and still more preferably hot-air drying involving a gas having a dew point of 20° C. to 90° C.

The drying step is, for an improved water absorbent property or color tone, carried out at a temperature controlled (by heating) so that the temperature is preferably 100° C. to 300° C., and more preferably 150° C. to 250° C. In particular, to improve both physical properties and whiteness of water absorbent resin to be produced, the drying step is preferably carried out at a temperature of 165° C. to 230° C. for a time period of not longer than 50 minutes, and more preferably 20 minutes to 40 minutes. In a case where the drying step is carried out through hot-air drying, the drying temperature is the temperature of the hot air. If the drying temperature or drying time period fails to fall within the above range, it is undesirable because such a failure may decrease the water absorption capacity without load (CRC) of water absorbent resin, increase the water-soluble component thereof, and/or decrease the whiteness thereof.

(2-4) Pulverization Step

This step is a step of pulverizing the dried polymer, produced through the drying step, to produce a pulverized polymer. In a case where the hydrogel produced through the polymerization step is in the form of particles (for example, the polymerization step is carried out through spray polymerization, droplet polymerization, reverse phase suspension polymerization, or the like), the pulverization step after the drying step may be omitted.

Equipment used for the pulverization step is not limited to any particular one. Examples of the equipment include a roll mill, a hammer mill, a roll granulator, a jaw crusher, a Jai Rectory crusher, a cone crusher, a roll crusher, and a cutter mill. The pulverization step preferably uses, among others, a multiple-stage roll mill or multiple-stage roll granulator for ease of particle size control.

(2-5) Classification Step

This step is a step of classifying the pulverized polymer, produced through the above steps (namely, the polymerization step, the gel crushing step, the drying step, and the pulverization step), to produce water absorbent resin powder.

The classification step of the present invention may be carried out through any method. Examples of the method include sieve classification involving a JIS standard sieve (JIS Z8801-1 (2000)). The particle sizes of water absorbent resin may be adjusted as appropriate through the polymerization step (in particular, reverse phase suspension polymerization or spray droplet polymerization) or another step (for example, the granulation step or fine powder recovery step) other than the classification step.

The classification step simply needs to be carried out at least once (at least one position) during the process of producing water absorbent resin. The classification step is, however, preferably carried out twice or more (two or more positions) during the production process, more preferably at least once (at least one position) immediately before or immediately after the surface-crosslinking step. The classification step may alternatively be carried out three to six times as necessary.

The water absorbent resin powder produced through the classification step has, as a particle size, a weight average particle diameter (D50) of preferably 200 μm to 600 μm, more preferably 200 μm to 550 μm, still more preferably 250 μm to 500 μm, and particularly preferably 300 μm to 450 μm. The water absorbent resin powder contains particles each having a diameter of less than 150 μm at a proportion of preferably 0 weight % to 10 weight %, more preferably 0 weight % to 5 weight %, and still more preferably 0 weight % to 1 weight %. The water absorbent resin powder contains particles each having a diameter of not less than 850 μm at a proportion of preferably 0 weight % to 5 weight %, more preferably 0 weight % to 3 weight %, and still more preferably 0 weight % to 1 weight %. The water absorbent resin powder has a particle size distribution having a logarithmic standard deviation ($\sigma\zeta$) of preferably 0.20 to 0.50, more preferably 0.25 to 0.40, and still more preferably 0.27 to 0.35. The particle size is measured with use of a standard sieve through a measurement method disclosed in, for example, PCT International Publication No. 2004/69915 or EDANA ERT 420.2-02.

The description above of the particle size applies not only to water absorbent resin before surface crosslinking, but also to surface-crosslinked water absorbent resin and water absorbent resin as a finished product. The water absorbent resin thus needs to be surface-crosslinked so that the particle size remains within the above range.

(2-6) Surface-Crosslinking Step

This step is a step of forming a portion with a high crosslinking density in a surface layer of the water absorbent resin powder produced through the above steps (that is, a portion of the water absorbent resin powder which portion is several tens of micrometers deep from the surface). The surface-crosslinking step includes the steps (2-6-1) to (2-6-4) below.

(2-6-1) Mixing Step

This step is a step of adding a surface-crosslinking agent (or an aqueous solution or dispersion liquid thereof) to the water absorbent resin powder and mixing the surface-crosslinking agent with the water absorbent resin powder. The mixture of the water absorbent resin powder and the surface-crosslinking agent may be referred to for convenience as "water absorbent resin mixture" (hereinafter referred to simply as "mixture") (which applies also to the description of the Examples).

(Surface-Crosslinking Agent)

The present invention may use any surface-crosslinking agent. Examples of the surface-crosslinking agent include compounds disclosed respectively in U.S. Pat. Nos. 6,228,930, 6,071,976, and 6,254,990.

More specifically, examples of the surface-crosslinking agent include (i) polyhydric alcohol compounds such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butandiol, 1,3-butandiol, 1,5-pentanediol, 1,6-hexanediol, and 1,2-cyclohexanedimethanol, (ii) epoxy compounds such as ethylene glycol diglycidyl ether and glycidol, (iii) polyhydric amine compounds such as ethylenediamine, diethylenetriamine, triethylenetetramine, tetraethylenepentamine, pentaethylenehexamine, polyethylene imine, and polyamide-polyamine, (iv) haloepoxy compounds such as epichlorohydrin, epibromhydrin, and α-methyl epichlorohydrin, (v) condensates of any of the above polyhydric amine compounds and any of the above haloepoxy compounds, (vi) oxazolidinone compounds such as 2-oxazolidinone, (vii) oxetane compounds such as methanesulfonic acid ((3-ethyloxetane-3-yl)methyl), chloromethanesulfonic acid ((3-ethyloxetane-3-yl)methyl), 1,6-bis(3-ethyloxetane-3-yl)-2,5-dioxahexane, and 1,12-bis(3-ethyloxetane-3-yl)-2,5,8,11-tetraoxadodecane, and (viii) alkylenecarbonate compounds such as ethylene carbonate. The present invention may use either only one of the above surface-crosslinking agents or two or more in combination.

The present invention, among the above examples, preferably uses an epoxy compound, a haloepoxy compound, an oxazolidinone compound, or an oxetane compound (each of which can react at a low temperature), more preferably an epoxy compound, a haloepoxy compound, or an oxetane compound, to improve physical properties of water absorbent resin and prevent a moisture content decrease during surface-crosslinking.

The surface-crosslinking agent is used in an amount of preferably 0.001 part by weight to 10 parts by weight, and more preferably 0.01 part by weight to 5 parts by weight, based on 100 parts by weight of the water absorbent resin powder in view of, for example, physical properties required of water absorbent resin. In a case where the present invention uses two or more of the above surface-crosslinking agents in combination, the total amount simply needs to fall within the above range.

The present invention may use water in mixing the surface-crosslinking agent with the water absorbent resin powder. Specifically, the surface-crosslinking agent may be in the form of an aqueous solution to be added to the water absorbent resin powder. The water may be used in an amount (that is, the water content of the aqueous solution) that is, although depending on the moisture content of the water absorbent resin powder, preferably 1 part by weight to 15 parts by weight, and more preferably 1 part by weight to 10 parts by weight, based on 100 parts by weight of the water absorbent resin powder.

The present invention may further use a hydrophilic organic solvent and/or a third substance as a mixing auxiliary agent in mixing the surface-crosslinking agent or an aqueous solution or dispersion liquid thereof with the water absorbent resin powder.

The hydrophilic organic solvent is not limited to any particular one. Examples of the hydrophilic organic solvent include (i) lower alcohol compounds such as methyl alcohol, ethyl alcohol, n-propyl alcohol, isopropyl alcohol, n-butyl alcohol, isobutyl alcohol, and t-butyl alcohol, (ii) ketone compounds such as acetone, (iii) ether compounds such as dioxane, tetrahydrofuran, and methoxy (poly)ethylene glycol, (iv) amide compounds such as ε-caprolactam and N,N-dimethylformamide, (v) sulfoxide compounds such as dimethyl sulfoxide, and (vi) polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butandiol, 1,4-butandiol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol.

For the present invention, a polyhydric alcohol compound is categorized as (i) a surface-crosslinking agent in a case where the polyhydric alcohol compound reacts with water absorbent resin and as (ii) a hydrophilic organic solvent in a case where the polyhydric alcohol compound does not react with water absorbent resin. Whether a polyhydric alcohol compound reacts may be easily determined with reference to (i) the amount of the polyhydric alcohol remaining or (ii) the amount of an increase of ester (for example, IR analysis).

The hydrophilic organic solvent is used in an amount of preferably not more than 10 parts by weight, and more preferably 0.1 part by weight to 5 parts by weight, based on 100 parts by weight of the solid content of the water absorbent resin powder.

Examples of the third substance include inorganic acids, organic acids, and polyamino acids (salts) disclosed in European Patent No. 0668080. These compounds may each function as a surface-crosslinking agent. A compound among the above compounds which does not degrade the water absorbent property of surface-crosslinked water absorbent resin is preferable. The third substance is used in an amount of preferably 0.005 part by weight to 10 parts by weight, and more preferably 0.05 part by weight to 5 parts by weight, based on 100 parts by weight of the solid content of the water absorbent resin powder.

(Adding/Mixing Method)

For the present invention, the surface-crosslinking agent (or an aqueous solution or dispersion liquid thereof) may be added and mixed through any method. For instance, either a surface-crosslinking agent and a solvent (water or a hydrophilic organic solvent) or a mixture thereof is prepared in advance, and is preferably sprayed or dropped, more preferably sprayed, onto the water absorbent resin powder to be mixed therewith.

The present invention may use any mixing apparatus for the above mixing. The present invention, however, preferably uses a high-speed stirring-type mixing apparatus, more preferably a high-speed stirring-type continuous mixing apparatus, and still more preferably a transverse-type or longitudinal-type high-speed stirring-type continuous mixing apparatus. Specifically, the present invention may use a Shugi mixer or Turbulizer (both available from Hosokawa Micron Corporation), a Lodige mixer (available from Gebruder Lodige Maschinenbau GmbH), or the like.

During the mixing step of the present invention, the mixing apparatus is operated with (i) a number of revolutions of preferably 100 rpm to 10000 rpm, and more preferably 300 rpm to 2000 rpm, and (ii) a retention time of preferably not longer than 180 seconds, more preferably 0.1 second to 60 seconds, and still more preferably 1 second to 30 seconds.

The water absorbent resin powder fed to the mixing step has a temperature of preferably 30° C. to 100° C., more preferably 35° C. to 80° C., and still more preferably 40° C. to 70° C. In a case where the water absorbent resin powder has a temperature within the above range, it is possible to prevent degradation of physical properties of water absorbent resin.

(2-6-2) Reaction Step

This step is a step (which may be referred to as "surface-crosslinking reaction step") of providing heat, an activation energy ray, or the like to the mixture, produced through the mixing step, to react the water absorbent resin with the surface-crosslinking agent to produce a reactant (hereinafter referred to for convenience as "water absorbent resin particles"; this applies also to the description of the Examples).

The present invention may as necessary include a storage step and/or a stirring step, each involving no reaction, between the mixing step and the reaction step to infiltrate or disperse the surface-crosslinking agent into the water absorbent resin powder before the reaction step.

(Reaction Apparatus)

This step may use a reaction apparatus that is identical in structure to the mixing apparatus used during the mixing step, but preferably uses an apparatus different in structure from the mixing apparatus used during the mixing step. Specifically, the reaction step preferably uses an apparatus that combines a publicly known dryer or heating furnace with a gas supply mechanism and/or gas discharge mechanism (hereinafter referred to also as "gas supply/discharge mechanism"). The reaction apparatus may be of a continuous type or batch type, but is preferably a continuous reaction apparatus for high productivity.

In a case where the reaction apparatus is of a batch type, the reaction apparatus preferably causes a surface-crosslinking reaction to occur through, for example, (i) a method of dispersing the mixture substantially equally on one or more trays, porous plates, or the like and heating the mixture, (ii) a method of filling, with the mixture, a single bath or plurality of baths equipped with a stirring blade or the like and heating the mixture while stirring the mixture, or (iii) heating the mixture while stirring the mixture on a fluidized bed.

In a case where the reaction apparatus is of a continuous type, the reaction apparatus preferably causes a surface-crosslinking reaction to occur through, for example, (i) a method of dispersing the mixture substantially equally on a belt, a porous plate, or the like and heating the mixture while conveying the mixture, (ii) a method of stirring the mixture with use of a stirring blade, a screw, or the like and heating the mixture while conveying the mixture, or (iii) a method of heating the mixture while conveying the mixture with use of an inclination of a heating surface.

The reaction apparatus may carry out heating through any method. Examples of the method include conductive heat transfer, radiative conduction, hot-air heat transfer, and dielectric heating, preferably conductive heat transfer and/or hot-air heat transfer, and more preferably conductive heat transfer. The reaction apparatus may use any heat source. Examples of the heat source include high-pressure steam (pressurized steam), warm water, niter (molten salt), and oil. Any of these examples may be selected as appropriate in view of the purpose and/or the like. The present invention particularly preferably uses a reaction apparatus of a conductive heat transfer type which reaction apparatus uses high-pressure steam (pressurized steam) as a heat source.

The reaction apparatus, in a case where it is of a continuous type in particular, is preferably further equipped with a mechanism for stirring and/or flowing the mixture (hereinafter referred to as "stirring/flowing mechanism") for an improved heating efficiency and a uniform surface-crosslinking reaction. The stirring/flowing mechanism is not limited to any particular one. Examples of the stirring/flowing mechanism include mechanisms of a groove stirring type, a screw type, a rotary type, a disc type, a kneading type, and a fluidized-bed type. The stirring/flowing mechanism is, among others, preferably (i) a stirring type mechanism including a stirring blade (paddle) or (ii) a stirring type mechanism (such as a rotary retort furnace) in which a heat transfer surface itself is movable. The reaction apparatus is particularly preferably of a paddle type.

The reaction apparatus, in a case where it is a continuous reaction apparatus of a conductive heat transfer type in particular, may have any heating surface area (heating area) that allows the powder temperature of the mixture to be controlled so that the powder temperature falls within the temperature range below. The heating surface area is, however, preferably 5 m$^2$/(t/hr) to 100 m$^2$/(t/hr), and more preferably 10 m$^2$/(t/hr) to 50 m$^2$/(t/hr), based on the amount of the mixture fed to be processed. The heating surface area being within the above range is preferable because such a heating surface area (i) facilitates controlling the powder temperature of the mixture and the temperature of an inner wall surface of the reaction apparatus so that those temperatures are each within the temperature range below and thus (ii) allows a stable operation.

The reaction apparatus, for a high efficiency in continuous production, preferably has an inclination that allows the mixture to spontaneously flow downward toward an outlet. Specifically, the inclination is preferably more than 0° and not more than 20°, and more preferably more than 0° and not more than 10°, downward relative to the horizontal plane. The inclination being more than 20° is not preferable because such an inclination will lead to an uneven reaction time, possibly degrading physical properties of water absorbent resin.

The reaction apparatus used for the present invention includes the above gas supply/discharge mechanism, which controls the dew point and temperature of the atmosphere in the reaction apparatus. The reaction apparatus preferably not merely has an air inlet and air outlet, but includes a blower or the like to adjust the amount and/or pressure of gas to be flown through the reaction apparatus. The reaction apparatus does not necessarily have only one air inlet and air outlet, and may have a plurality of air inlets and a plurality of air outlets in correspondence with the size of the reaction apparatus, and the dew point and temperature of the atmosphere in the reaction apparatus.

The present invention may alternatively use a combination of a plurality of reaction apparatuses that either share the same heating method, stirring method, gas supplying method, and/or gas discharge method or have different heating methods, stirring methods, gas supplying methods, and/or gas discharge methods.

(Airflow)

The present invention, in order for the dew point and temperature of the atmosphere in the reaction apparatus to be each stably within the range below, preferably controls an airflow in the reaction apparatus so that air flows in a fixed direction. The expression "fixed direction" indicates not that air flows in an identical direction at any position, but that the direction of the airflow does not change macroscopically. The airflow control for the present invention does not cover, for example, partial and/or temporary turbulence or swirl occurring in the airflow due to stirring or the like. Air does not flow in a "fixed direction" if an airflow caused by air intake at an air inlet and air discharge at an air outlet has been changed during a surface-crosslinking reaction to an airflow caused by an air intake at the air outlet and an air discharge at the air inlet.

The dew point and temperature of the atmosphere during this step refers to the average dew point and average temperature of gas present in a space above a mixture in the reaction apparatus. The dew point and temperature of the atmosphere are preferably measured at a position vertically above a mixture being heated at a heated portion inside the reaction apparatus. The dew point and temperature of the atmosphere may each fall outside the range below (i) immediately after the start of a surface-crosslinking reaction or, (ii) in the case where the reaction apparatus is of a continuous type, immediately after the mixture is put into the heated portion or immediately before the mixture is discharged from the heated portion.

In a case where the reaction apparatus for the present invention has a plurality of air inlets and a plurality of air outlets, in particular in a case where the reaction apparatus is of a continuous type, air flows in preferably a vertical or horizontal direction, more preferably a horizontal direction, still more preferably the airflow is a countercurrent and/or cocurrent, and particularly preferably a cocurrent, based on the direction of movement of a mixture put into the reaction apparatus. The airflow may have a countercurrent and a cocurrent simultaneously in the reaction apparatus at individual portions thereof as long as the direction of the airflow does not change over time.

The airflow may have any flow amount that allows the dew point and temperature of the atmosphere in the reaction apparatus to be controlled so that the dew point and temperature each fall within a desired range. The flow amount is at least more than 0.1 (Nm$^3$/hr), preferably not more than 10000 (Nm$^3$/hr), more preferably not more than 5000 (Nm$^3$/hr), and still more preferably not more than 3000 (Nm$^3$/hr). The airflow has, relative to the amount of a mixture to be processed, a rate of preferably not more than 3000 (Nm$^3$/t), and more preferably not more than 1000 (Nm$^3$/t). The expression "Nm$^3$" indicates the volume of gas which volume has been converted into a measurement under standard conditions (at 0° C. and 1 atmosphere), and does not indicate the volume of gas present at 0° C. and 1 atmosphere.

The flow amount and rate of the airflow are each a value defined by (i) the total flow amount of gas discharged and/or (ii) a combination of the flow amount and the amount of water absorbent resin powder fed to the surface-crosslinking step. The flow amount and rate of the airflow may each fall outside the above range if the continuous production does not have a steady state, for example, at the start or stop of an operation.

The reaction apparatus may accept the introduction of any gas that allows the dew point of the atmosphere to be controlled so that the dew point falls within the range below. Examples of the gas include (i) inert gases such as air, dry air, nitrogen, helium, and argon, (ii) mixtures of water vapor and any of the above inert gases, and (iii) steam. Any of the above gases may be heated or cooled, and may be under pressure or under reduced pressure. The reaction apparatus may be typically fed with air having a temperature of 0° C. to 50° C. at a substantially atmospheric pressure (preferably 1 atmosphere (101.3 kPa)±10%, more preferably 1 atmosphere±5%, and still more preferably 1 atmosphere±1%).

The reaction apparatus preferably has a slightly reduced internal pressure. Specifically, the internal pressure is different from the atmospheric pressure by preferably −10 kPa to 0 kPa, more preferably −5 kPa to 0 kPa, and still more preferably −2 kPa to 0 kPa.

(Operation Conditions)

The present invention, to produce its advantages, characteristically (i) controls the temperature of the inner wall surface of the reaction apparatus for use during the reaction step so that the temperature is 100° C. to 250° C., (ii) controls the dew point of the atmosphere in the reaction apparatus so that the dew point is 60° C. to 100° C., and (iii) heat-treats a water absorbent resin mixture to control the powder temperature so that the powder temperature is 90° C. to 130° C. The description below deals in detail with operation conditions during the reaction step.

The reaction apparatus, during the reaction step, heat-treats the mixture to control its powder temperature so that the powder temperature falls within a desired temperature range. The powder temperature is essentially 90° C. to 130° C., preferably 95° C. to 125° C., and more preferably 100° C. to 120° C. If the powder temperature is lower than 90° C., there may be an insufficiency of covalent bonds for forming a surface-crosslinked layer. A powder temperature of higher than 130° C. is not preferable because such a high powder temperature will let a large amount of moisture evaporate from the water absorbent resin at a high evaporation rate, which in turn makes it impossible to produce water absorbent resin having a desired moisture content.

The powder temperature of the mixture corresponds to the highest temperature during the reaction step. In the case where the reaction apparatus is of a continuous type, the powder temperature is estimated from the temperature of water absorbent resin particles occurring immediately after being discharged from the reaction apparatus (that is, a reactant resulting from heat-treating a mixture of the water absorbent resin powder and the surface-crosslinking agent).

Controlling the powder temperature on the basis of (i) the temperature of the inner wall surface of the reaction apparatus, (ii) the heating surface area of the reaction apparatus, and (iii) the retention time allows production of water absorbent resin having a desired moisture content and desired water absorbing ability.

The reaction apparatus, for a stable production, has an inner wall surface whose temperature is controlled so that the temperature is essentially 100° C. to 250° C., preferably 105° C. to 200° C., and more preferably 110° C. to 150° C. If the temperature of the inner wall surface is lower than 100° C., there will occur condensation on an inner surface of the reaction apparatus, which will in turn cause water absorbent resin to adhere to the inner surface. This may decrease the productivity or degrade physical properties. If the temperature of the inner wall surface is higher than 250° C., there will occur partial excessive heating. This may degrade physical properties, which is not preferable. The temperature of the inner wall surface of the reaction apparatus may be controlled by means of the heat source described above and heating method.

The time of retention (heat treatment time) in the reaction apparatus is not limited to any particular length as long as the powder temperature falls within the above range. The retention time is typically 5 minutes to 60 minutes, and preferably 10 minutes to 50 minutes.

The reaction apparatus for use during the reaction step has an internal atmosphere whose dew point is controlled so that the dew point is essentially 60° C. to 100° C., and preferably 65° C. to 95° C. A dew point of the atmosphere of lower than 60° C. will let a large amount of moisture evaporate from the water absorbent resin at a high evaporation rate, which in turn makes it impossible to produce water absorbent resin having a desired moisture content. Further, there will be an insufficiency of infiltration of the surface-crosslinking agent into water absorbent resin, which will in turn result in a decrease in the water absorbing ability under pressure.

The reaction apparatus for use during the reaction step has an internal atmosphere whose temperature is controlled so that the temperature is preferably 100° C. to 150° C., and more preferably 105° C. to 145° C. A temperature of the atmosphere of lower than 100° C. will let condensation of moisture evaporating from water absorbent resin occur on the inside of a heating device, which will in turn cause water absorbent resin to adhere to the inside of the heating device. This may prevent a stable continuous production, and also decrease the productivity and/or degrade physical properties.

The dew point and temperature of the atmosphere may be controlled by appropriately controlling, for example, the amount of supply of gas, the amount of discharge of gas, the temperature of the gas, and/or the dew point of the gas in view of, for example, a heat transfer from the inner wall surface of the reaction apparatus, a heat transfer from water absorbent resin, and a rise of the dew point due to water vapor generated from water absorbent resin. Specifically, the dew point and temperature of the atmosphere may be adjusted through, for example, (i) a method of equipping the reaction apparatus with a measuring device and feeding the gas as necessary or (ii) a method of, for example, changing the amount of discharge of gas and/or the pressure of the gas. The present invention may combine a plurality of control methods as appropriate.

The dew point and temperature of the atmosphere in the reaction apparatus may each vary depending on the position of the heated portion or passage of processing time. The dew point and temperature of the atmosphere in the reaction apparatus are, however, desirably controlled so that the dew point and temperature of the atmosphere are each within a fixed range. The expression "within a fixed range" indicates that (i) the dew point and temperature of the atmosphere are each within the corresponding range above over a period of preferably not less than 50%, more preferably not less than 70%, and still more preferably not less than 80%, of the entire time of the heat treatment and that (ii) the degree of the variation is preferably not more than 20° C., more preferably not more than 10° C., still more preferably not more than 5° C., and particularly preferably not more than 2° C.

In a case where the airflow has a flow amount within the above range, the dew point and temperature of the atmosphere in the reaction apparatus, which are defined for the present invention, may be a dew point and temperature at a suitable measurement position in the gas discharge mechanism of the reaction apparatus. This case, however, requires that (i) no other gas should flow in between the heated portion and measurement position of the reaction apparatus, that (ii) no process should be carried out by, for example, a gas washer, that (iii) there should be no temperature change forced with use of a heater, a cooler, or the like, and that (iv) gas should move from the heated portion of the reaction apparatus to the measurement position thereof within 1 second.

The present invention has a powder relative humidity of preferably 15% to 100%, more preferably 20% to 80%, and still more preferably 22% to 70%. A powder relative humidity of less than 15% will let moisture evaporate from water absorbent resin at a high evaporation rate, which will in turn make it impossible to produce water absorbent resin having a desired moisture content. If the powder relative humidity is more than 100%, there will occur condensation on a surface of water absorbent resin, which will in turn cause water absorbent resin particles to agglomerate into a lump. This will undesirably prevent a stable production and degrade physical properties as a result.

(2-6-3) Cooling Step (Optional)

This step is an optional step carried out after the surface-crosslinking reaction step to, for example, stop the surface-crosslinking reaction described above or convey water absorbent resin to a subsequent step.

The present invention preferably feeds the water absorbent resin particles, produced through the reaction step, to the cooling step within a short time. The time is preferably longer than 0 seconds and not longer than 3 minutes, more preferably longer than 0 seconds and not longer than 2 minutes, still more preferably longer than 0 seconds and not longer than 1 minute, and particularly preferably longer than 0 seconds and not longer than 30 seconds. The time may be controlled by means of, for example, (i) direct coupling or short-distance connection (for example, within 10 m) between the heating device for the reaction step and a cooling device for the cooling step or (ii) a layout of the two devices.

The cooling device for use during this step is not limited to any particular one, and may be, for example, a stirring apparatus or fluidization apparatus having a cooling function involving use of a heat transfer surface, an airflow, or the like. Specifically, the cooling device may be a device that is identical in structure to the paddle-type heating device preferably used during the reaction step and that uses a coolant instead of a heat medium. The cooling device has a size set as appropriate in view of, for example, cooling efficiency, and does not necessarily have a size equal to that of the reaction apparatus.

The coolant for the cooling device is not limited to any particular one, and may be, for example, water, warm water, or an antifreezing liquid. The cooling temperature for the cooling device (that is, the temperature of a heat transfer surface such as a jacket) is preferably 0° C. to 90° C., more preferably 20° C. to 85° C., and still more preferably 40° C. to 80° C.

(2-6-4) Adding Step (Optional)

This step is a step of adding an additive to water absorbent resin to, for example, improve its physical properties, and is a step optionally carried out as necessary.

The adding step may be carried out after the reaction step, or in a case where the cooling step is carried out, the adding step may be carried out after the cooling step or may be combined with the cooling step (that is, a step of cooling water absorbent resin and adding an additive thereto simultaneously with use of a single device). In a case where the cooling step is not carried out, the device for adding an additive is not limited to any particular one, and may preferably be a stirring apparatus or a fluidization apparatus. The device for adding an additive may preferably be, as a stirring apparatus, a stirring and mixing apparatus disclosed in PCT International Publication No. 2008/141821.

(Additive)

The present invention, to impart various additional functions to water absorbent resin to be produced, preferably involves adding any of various additives below, more preferably involves adding any of such additives in the form of a water-based liquid in which the additive is dissolved or dispersed.

The additive is not limited to any particular one. Examples of the additive include a deodorant agent, an antibacterial agent, an anti-coloring agent, a chelating agent, an inorganic monovalent or polyvalent salt, an acidic compound, a reducing agent, an alkaline compound, and a surfactant. Among these examples, a water-soluble additive is preferable. The additive is more preferably a water-soluble additive selected from a chelating agent, an inorganic reducing agent, a polyhydric metal salt, and a deodorant agent. The additive is either only one or a combination of two or more selected from the above examples depending on the purpose.

Specifically, the additive is preferably a chelating agent to prevent coloring, and degradation (urine resistance) of water absorbent resin to be produced. The chelating agent for the present invention is, for example, any of various chelating agents disclosed under "[2] Chelating Agent" of PCT International Publication No. 2011/040530, and is used in an amount disclosed thereunder. The additive is, among those chelating agents disclosed, preferably a water-soluble, non-polymeric amino polyvalent carboxylic acid or amino polyvalent phosphoric acid, or a salt thereof (in particular, a monovalent salt).

Further, the additive is preferably an inorganic reducing agent to prevent coloring, degradation, reduce a residual monomer of water absorbent resin to be produced. The inorganic reducing agent for the present invention is, for example, any of various inorganic reducing agents disclosed under "[3] Inorganic Reducing Agent" of PCT International Publication No. 2011/040530, and is used in an amount disclosed thereunder. The inorganic reducing agent is, among those inorganic reducing agents disclosed, preferably a water-soluble phosphoric reducing agent or sulfuric reducing agent, and more preferably a sulfite such as sodium bisulfite (SBS).

Further, the additive is preferably an inorganic salt, in particular a polyhydric metal salt and/or cationic polymer to improve the water absorption speed (Vortex) and liquid permeability (SFC) of water absorbent resin to be produced and to impart fluidity to the water absorbent resin during moisture absorption. The polyhydric metal salt and/or cationic polymer for the present invention is, for example, any of various polyhydric metal salts and/or cationic polymers disclosed under "[6] Polyhydric Metal Salt and/or Cationic Polymer" of PCT International Publication No. 2011/040530, and is used in an amount disclosed thereunder. The polyhydric metal salt and/or cationic polymer is, among those various polyhydric metal salts and/or cationic polymers disclosed, preferably an inorganic salt of aluminum.

The deodorant agent is not limited to any particular one, and may be, for example, a synthetic or natural deodorant agent. Specifically, the deodorant agent is preferably a deodorant agent derived from a plant component disclosed in PCT International Publication No. 2003/104349. More specifically, the deodorant agent is a polyphenol such as tannin.

In a case where the additive is used in the form of a water-based liquid, the total additive concentration is preferably 0.01 weight % to 50 weight %, more preferably 0.1 weight % to 40 weight %, and still more preferably 1 weight % to 30 weight %. The additive is added in any amount set as appropriate depending on the purpose and/or the like based on water absorbent resin. The total additive amount is preferably 1 ppm to 10 weight %, more preferably 10 ppm to 1 weight %, and still more preferably 20 ppm to 0.5 weight %.

(2-7) Steps after Addition (Sizing Step, Etc)

The present invention may further include a separate, curing step of partially drying or heating the water absorbent resin after the addition of the water-based liquid to adjust the moisture content and improve the powder fluidity. The curing step does not necessarily dry the water absorbent resin (decrease the moisture content), but simply needs to heat-treat the water absorbent resin. The curing step, through the heat treatment, allows the moisture added to infiltrate the water absorbent resin, and thus improves the powder fluidity. This in turn advantageously improves, for example, (i) ease of handling during subsequent steps of the production process such as a product filling step and (ii) product stability in storage.

The present invention includes adding the water-based liquid during the reaction step and/or a step after the reaction step. This allows moisture to infiltrate water absorbent resin for powder fluidity, and thus does not require a curing step. This in turn allows the process to be simplified, and reduces physical property degradation caused by a process damage. The powder fluidity has a flow rate as defined in ERT 450.2-02 which flow rate is preferably not less than 3 (g/s), more preferably not less than 5 (g/s), and still more preferably not less than 7 (g/s).

The production process may, for example, generate agglomerates and/or change the particle sizes as a result of the surface crosslinking or addition of the water-based liquid. The present invention may thus further include a classification step and an optional, agglomerate pulverizing step (collectively referred to as "sizing step"). The present invention preferably includes a sizing step, and more preferably further removes agglomerates (coarse particles) or fine powder during the classification step. Such agglomerates or fine powder (in particular, particles each having a size of less than 150 μm) removed during the classification step may be discarded. The agglomerates may alternatively be pulverized (grinded). The fine powder may alternatively be recycled.

(2-8) Other Steps

The present invention may further include, other than the above steps, such steps as a step of recycling an evaporated monomer, a granulation step, and a fine powder recycling step as necessary.

The present invention may further include a step of adding, for example, an oxidizing agent, a chelating agent, an antioxidant, water, a polyhydric metal compound, water-insoluble inorganic or organic powder such as silica or metal soap, a deodorant agent, an antibacterial agent, a polymer polyamine, pulp, or thermoplastic fiber in an amount of preferably 0 parts by weight to 3 parts by weight, and more preferably 0 parts by weight to 1 parts by weight, based on 100 parts by weight of the water absorbent resin so that, for example, the color tone is stable over time and that gel degradation is prevented.

[3] Physical Properties of Polyacrylic Acid (Salt)-Based Water Absorbent Resin The polyacrylic acid (salt)-based water absorbent resin produced through the method of the present invention is, in a case where it is used for a sanitary product, in particular a disposable diaper, desirably arranged such that at least one physical property among (3-1) to (3-5) below, more preferably two or more physical properties including the water absorption capacity under load (AAP), or still more preferably three or more physical properties are controlled so that those physical properties are each within a desired range.

Examples of the physical properties controlled other than (3-1) to (3-5) below include FSC (free swell capacity), PSD (particle size distribution), pH, flow rate, density (bulk specific gravity), respirable particles (respirable dust), dust, and the like.

The present invention is preferably applied to a production method in which the above physical properties are highly controlled. If a physical property does not fall within the corresponding range below, the present invention merely produces insufficient effects, or fails to allow sufficient performance to be exhibited for a high-concentration disposable diaper, which requires a large per-unit amount of water absorbent resin.

Physical properties to be controlled, and a method for measuring the physical properties are determined as appropriate. The EDANA measurement methods described above may be used for the production of the polyacrylic acid (salt)-based water absorbent resin of the present invention.

(3-1) Water Absorption Capacity without Load (CRC)

The polyacrylic acid (salt)-based water absorbent resin of the present invention has a water absorption capacity without load (CRC) of preferably not less than 10 (g/g), more preferably not less than 20 (g/g), still more preferably not less than 25 (g/g), particularly preferably not less than 27 (g/g). A larger value of the water absorption capacity without load (CRC) is preferable. The water absorption capacity without load (CRC) has no particular upper limit value. The water absorption capacity without load (CRC) is, however, preferably not more than 50 (g/g), more preferably not more than 40 (g/g), still more preferably not more than 38 (g/g), for a balance between other physical properties and itself.

(3-2) Water Absorption Capacity Under Load (AAP)

The polyacrylic acid (salt)-based water absorbent resin of the present invention has a water absorption capacity under load (AAP) (under load of 2.06 kPa) of preferably not less than 20 (g/g), more preferably not less than 22 (g/g), even more preferably not less than 23 (g/g), particularly preferably not less than 25 (g/g), most preferably not less than 28 (g/g), for prevention of leakage from a disposable diaper. A larger value of the water absorption capacity under load (AAP) is preferable. The water absorption capacity under load (AAP) has no particular upper limit value. The water absorption capacity under load (AAP) is, however, preferably not more than 40 (g/g), more preferably not more than 35 (g/g), for a balance between other physical properties and itself.

(3-3) Moisture Content

The polyacrylic acid (salt)-based water absorbent resin of the present invention has a moisture content of preferably 6 weight % to 20 weight %, more preferably 6 weight % to 18 weight %, still more preferably 6 weight % to 15 weight %. A moisture content within the above range not only allows production of water absorbent resin that generates only a small amount of fine powder and that is excellent in impact resistance, but also improves the productivity.

(3-4) Water-Soluble Component (Ext)

The polyacrylic acid (salt)-based water absorbent resin of the present invention has a water-soluble component (Ext) of preferably not more than 35 weight %, more preferably not more than 25 weight %, still more preferably not more than 15 weight %, particularly preferably not more than 10 weight %. The water-soluble component (Ext) is controllable on the basis of, for example, the above polymerization conditions (such as the amount of the crosslinking agent) and/or drying condition (drying temperature).

(3-5) Dusting Rate

The polyacrylic acid (salt)-based water absorbent resin of the present invention has a dusting rate of preferably 0 weight % to 2.0 weight %, more preferably 0 weight % to 1.5 weight %, still more preferably 0 weight % to 1.0 weight %. A dusting rate of more than 2.0 weight % may let dust be generated during the process of producing or conveying water absorbent resin of the present invention, and may thus degrade the working environment.

[4] Applications of Polyacrylic Acid (Salt)-Based Water Absorbent Resin

The polyacrylic acid (salt)-based water absorbent resin of the present invention is not particularly limited in terms of application, and is preferably used as an absorbent body for use in an absorbent article such as a disposable diaper, a sanitary napkin, or an incontinence pad. The polyacrylic acid (salt)-based water absorbent resin exhibits its excellent performance in a case where (i) the polyacrylic acid (salt)-based water absorbent resin is used in a high-concentration disposable diaper in particular that has problematically suffered from odor, coloring and the like arising from a raw material or further in a case where (ii) the polyacrylic acid (salt)-based water absorbent resin is used in an upper layer of an absorbent body in an absorbent article.

The absorbent body may include an absorbent material such as pulp fiber as an optional component. In this case, the absorbent body contains the water absorbent resin in an amount (core concentration) of preferably 30 weight % to 100 weight %, more preferably 40 weight % to 100 weight %, still more preferably 50 weight % to 100 weight %, further still more preferably 60 weight % to 100 weight %, particularly preferably 70 weight % to 100 weight %, most preferably 75 to 95 weight.

EXAMPLES

The Examples section below describes the present invention in greater detail. The present invention should, however, not be narrowly interpreted within the limits of the Examples. Any proper combination of technical means disclosed in different Examples is encompassed in the scope of the present invention.

Unless otherwise noted, electric appliances used in the Examples and the like (including an apparatus for measuring physical properties) used a 200 V or 100 V power supply, and the physical properties of water absorbent resin were measured at room temperature (20° C. to 25° C.) and a relative humidity of 50% RH. The Examples section below may, for convenience, use (i) the symbol "l" or "L" to mean "liter" and (ii) the symbol "wt %" to mean "weight %".

[Measurement of Physical Properties of Water Absorbent Resin]

(a) Moisture Content

The moisture content of water absorbent resin (including, for example, a mixture as an intermediate) produced through the method of the present invention was measured in conformity to ERT 430.2-02. For the present invention, the amount of a sample was changed to 1.0 g, and the drying temperature was changed to 180° C.

(b) Water Absorption Capacity without Load (CRC)

The water absorption capacity without load (CRC) of water absorbent resin produced through the method of the present invention was measured in conformity to ERT 441.2-02.

(C) Water Absorption Capacity Under Load (AAP)

The water absorption capacity under load (AAP) of water absorbent resin produced through the method of the present invention was measured in conformity to ERT 442.2-02.

(d) Dusting Rate

The dusting rate of water absorbent resin produced through the method of the present invention was measured on the basis of the damage test below (paint shaker (PS) test).

Specifically, (i) 30 g of the water absorbent resin and (ii) 10 g of glass beads each having a diameter of 6 mm were put into a glass vessel having a diameter of 6 cm and a height of 11 cm. The glass vessel was attached to a paint shaker (No. 488, available from Toyo Seiki Seisaku-sho, Ltd.). The paint shaker was then shaken at 800 (cycle/min) (CPM) for 60 minutes and stopped. Next, the water absorbent resin and the glass beads were separated from each other with use of a JIS standard sieve having a mesh size of 2 mm. Japanese Patent Application Publication, Tokukaihei, No. 9-235378 A (1997) describes a paint shaker in detail.

The dusting rate is calculated through the equation below.

Dusting rate (weight %)=(Amount of component with particle diameters of not larger than 150 μm after PS)−(Amount of component with particle diameters of not larger than 150 μm before PS)

Production Example 1

A monomer aqueous solution (a) was prepared to contain an acrylic acid, a 48.5 weight % sodium hydroxide aqueous solution, ion-exchange water, polyethylene glycol diacrylate (9 ethylene oxide units on average) as an internal crosslinking agent, and ethylenediamine pentaacetate trisodium as a chelating agent. The monomer aqueous solution (a) had a monomer concentration of 43 weight % and a neutralization rate of 75 mol %. The internal crosslinking agent and the chelating agent were used in respective amounts of 0.02 mol % and 100 ppm based on the monomer.

Next, the monomer aqueous solution (a) was heated. When the liquid temperature reached 95° C., sodium persulfate as a polymerization initiator was added to the monomer aqueous solution (a) in an amount of 0.05 mol % based on the monomer, and was mixed therein. The resulting monomer aqueous solution (a) was then continuously supplied to a polymerization device of a continuous belt type. Thirty seconds after the supply, polymerization started, to produce sheet-shaped hydrogel-like crosslinked polymer (a).

The sheet-shaped hydrogel-like crosslinked polymer (a) produced through the above operation was gel-crushed with use of a meat chopper, to produce particulate hydrogel-like crosslinked polymer (a). The particulate hydrogel-like crosslinked polymer (a) was then spread thinly on a porous plate of a band dryer, and was dried with hot-air at 180° C. for 40 minutes, to thereby produce block-shaped dried polymer (a). Next, the dried polymer (a) was continuously supplied into a roll mill and pulverized therein, and was then continuously classified with use of a classification apparatus provided with JIS standard sieves having respective mesh sizes of 850 μm and 150 μm.

The above series of operations produced water absorbent resin powder (A) made up of particles (i) each with a diameter of not less than 150 μm and less than 850 μm and (ii) having a content of not less than 90 weight %. The water absorbent resin powder (A) thus produced had a weight average particle diameter (D50) of 380 μm, a water absorption capacity without load (CRC) of 51 (g/g), and a moisture content of 5.1 weight %.

Example 1

The water absorbent resin powder (A) produced in Production Example 1 above was continuously supplied to a high-speed stirring-type mixing apparatus (Turbulizer, available from Hosokawa Micron Corporation) in a processing amount of 50 (kg/hr). Next, a surface-crosslinking agent solution (1) prepared in advance was added to the mixing apparatus and mixed therein, to produce a dampened mixture (1). The surface-crosslinking agent solution (1) was a mixture of 0.015 part by weight of ethylene glycol diglycidyl ether, 1.0 part by weight of propylene glycol, and 3.0 parts by weight of ion-exchange water based on 100 parts by weight of the water absorbent resin powder (A).

The mixture (1) produced through the above operation was continuously supplied to a paddle-type indirect heating reactor (paddle dryer, available from Nara Machinery Co., Ltd.) adjusted to have a temperature of the atmosphere of 130° C. and a dew point of the atmosphere of 80° C. (relative humidity of 18% RH) for a surface-crosslinking reaction. The paddle dryer had (i) an inner wall surface (paddle and jacket) heated with use of a heat medium having a temperature of 120° C. and (ii) a top plate having a temperature retained with use of vapor of 0.2 MPa (approximately 120° C.). The surface-crosslinking reaction involved a heat treatment time of 42 minutes. Water absorbent resin particles (1) immediately after being discharged from the paddle dryer had a temperature of 101° C.

Next, the water absorbent resin particles (1) discharged from the paddle dryer were passed through a JIS standard sieve having a mesh size of 850 μm and were sized, to produce water absorbent resin (1). The water absorbent resin (1) thus produced had a moisture content of 7.9 weight %. Other physical properties are shown in Table 1.

Example 2

An operation similar to that of Example 1 above was conducted except that the temperature of the atmosphere in the paddle dryer was adjusted to 109° C. and that the dew point of the atmosphere in the paddle dryer was adjusted to 65° C. (relative humidity of 18% RH), to thereby produce water absorbent resin (2). The water absorbent resin (2) thus produced had a moisture content of 6.8 weight %. Other physical properties are shown in Table 1.

The water absorbent resin particles (2) immediately after being discharged from the paddle dryer had a temperature of 101° C.

Comparative Example 1

An operation similar to that of Example 1 above was conducted except that the temperature of the atmosphere in the paddle dryer was adjusted to 83° C. and that the dew point of the atmosphere in the paddle dryer was adjusted to 45° C. (relative humidity of 18% RH), to thereby produce comparative water absorbent resin (1). The comparative water absorbent resin (1) thus produced had a moisture content of 4.9 weight %. Other physical properties are shown in Table 1.

The comparative water absorbent resin particles (1) immediately after being discharged from the paddle dryer had a temperature of 100° C.

Comparative Example 2

An operation similar to that of Example 1 above was conducted except that the temperature of the heat medium was raised, to thereby produce comparative water absorbent resin (2). The comparative water absorbent resin (2) thus produced had a moisture content of 1.2 weight %. Other physical properties are shown in Table 1.

The comparative water absorbent resin particles (2) immediately after being discharged from the paddle dryer had a temperature of 195° C.

Example 3

The water absorbent resin powder (A) produced in Production Example 1 above was continuously supplied to a high-speed stirring-type mixing apparatus (Turbulizer, available from Hosokawa Micron Corporation) in a processing amount of 100 (kg/hr). Next, a surface-crosslinking agent solution (3) prepared in advance was added to the mixing apparatus and mixed therein, to produce a dampened mixture (3). The surface-crosslinking agent solution (3) was a mixture of 0.03 part by weight of ethylene glycol diglycidyl ether, 1.0 part by weight of propylene glycol, and 4.0 parts by weight of ion-exchange water based on 100 parts by weight of the water absorbent resin powder (A).

The mixture (3) produced through the above operation was continuously supplied to a paddle-type indirect heating reactor (paddle dryer, available from Nara Machinery Co., Ltd.) adjusted to have a temperature of the atmosphere of 145° C. and a dew point of the atmosphere of 95° C. (relative humidity of 20% RH) for a surface-crosslinking reaction. The paddle dryer had (i) an inner wall surface (paddle and jacket) heated with use of a heat medium having a temperature of 145° C. and (ii) a top plate having a temperature retained with use of vapor of 0.2 MPa (approximately 120° C.). The surface-crosslinking reaction involved a heat treatment time of 21 minutes. Water absorbent resin particles (3) immediately after being discharged from the paddle dryer had a temperature of 119° C.

Next, the water absorbent resin particles (3) discharged from the paddle dryer were passed through a JIS standard sieve having a mesh size of 850 µm and were sized, to produce water absorbent resin (3). The water absorbent resin (3) thus produced had a moisture content of 8.5 weight %. Other physical properties are shown in Table 1.

Comparative Example 3

An operation similar to that of Example 3 above was conducted except that the temperature of the atmosphere in the paddle dryer was adjusted to 80° C. and that the dew point of the atmosphere in the paddle dryer was adjusted to 55° C. (relative humidity of 33% RH), to thereby produce comparative water absorbent resin (3). The comparative water absorbent resin (3) thus produced had a moisture content of 4.7 weight %. Other physical properties are shown in Table 1.

The comparative water absorbent resin particles (3) immediately after being discharged from the paddle dryer had a temperature of 118° C.

Example 4

The water absorbent resin powder (A) produced in Production Example 1 above was continuously supplied to a high-speed stirring-type mixing apparatus (Turbulizer, available from Hosokawa Micron Corporation) in a processing amount of 40 (kg/hr). Next, a surface-crosslinking agent solution (4) prepared in advance was added to the mixing apparatus and mixed therein, to produce a dampened mixture (4). The surface-crosslinking agent solution (4) was a mixture of 0.03 part by weight of glycerol polyglycidyl ether, 1.0 part by weight of propylene glycol, and 4.0 parts by weight of ion-exchange water based on 100 parts by weight of the water absorbent resin powder (A).

The mixture (4) produced through the above operation was continuously supplied to a paddle-type indirect heating reactor (paddle dryer, available from Nara Machinery Co., Ltd.) adjusted to have a temperature of the atmosphere of 135° C. and a dew point of the atmosphere of 85° C. (relative humidity of 18% RH) for a surface-crosslinking reaction. The paddle dryer had (i) an inner wall surface (paddle and jacket) heated with use of a heat medium having a temperature of 125° C. and (ii) a top plate having a temperature retained with use of vapor of 0.2 MPa (approximately 120° C.). The surface-crosslinking reaction involved a heat treatment time of 53 minutes. Water absorbent resin particles (4) immediately after being discharged from the paddle dryer had a temperature of 111° C.

Next, the water absorbent resin particles (4) discharged from the paddle dryer were passed through a JIS standard sieve having a mesh size of 850 µm and were sized, to produce water absorbent resin (4). The water absorbent resin (4) thus produced had a moisture content of 7.5 weight %. Other physical properties are shown in Table 1.

Comparative Example 4

An operation similar to that of Example 4 above was conducted except that the dew point of the atmosphere in the paddle dryer was adjusted to 35° C. (relative humidity of 2% RH), to thereby produce comparative water absorbent resin (4). The comparative water absorbent resin (4) thus produced had a moisture content of 2.8 weight %. Other physical properties are shown in Table 1.

The comparative water absorbent resin particles (4) immediately after being discharged from the paddle dryer had a temperature of 110° C.

Example 5

Aerosil 200 (available from Nippon Aerosil Co., Ltd.) was further added to the water absorbent resin (1) produced in Example 1 above, and was mixed therein, to thereby produce water absorbent resin (5). The water absorbent resin (5) thus produced had a moisture content of 7.9 weight %. Other physical properties are shown in Table 1.

The Aerosil 200 was used in an amount of 0.5 part by weight based on 100 parts by weight of the water absorbent resin (1). The above mixing was carried out with use of a Lodige mixer (available from GmbH) for 5 minutes.

Comparative Example 5

Aerosil 200 (available from Nippon Aerosil Co., Ltd.) was further added to the comparative water absorbent resin (1) produced in Comparative Example 1 above, and was mixed therein, to thereby produce comparative water absorbent resin (5). The comparative water absorbent resin (5) thus produced had a moisture content of 4.9 weight %. Other physical properties are shown in Table 1.

The Aerosil 200 was used in an amount of 0.5 part by weight based on 100 parts by weight of the comparative water absorbent resin (1). The above mixing was carried out with use of a Lodige mixer (available from GmbH) for 5 minutes.

Example 6

An aluminum sulfate aqueous solution was further added to the water absorbent resin (1) produced in Example 1 above, and was mixed therein. The resulting water absorbent resin (1) was then dried and sized, to thereby produce water absorbent resin (6). The water absorbent resin (6) thus produced had a moisture content of 8.0 weight %. Other physical properties are shown in Table 1.

The aluminum sulfate aqueous solution was a mixture of a 27 weight % aluminum sulfate aqueous solution (8 weight % based on aluminum oxide), a 60 weight % sodium lactate aqueous solution, and 1,2-propylene glycol at a mixing ratio (weight ratio) of 1.0:0.3:0.025. The aluminum sulfate aqueous solution was added in an amount of 2.5 parts by weight based on 100 parts by weight of the water absorbent resin (1).

The above drying was carried out in a windless state at 60° C. for 1 hour. The above sizing involved use of a JIS standard sieve having a mesh size of 850 μm.

Comparative Example 6

An aluminum sulfate aqueous solution was further added to the comparative water absorbent resin (1) produced in Comparative Example 1 above, and was mixed therein. The resulting comparative water absorbent resin (1) was then dried and sized, to thereby produce comparative water absorbent resin (6). The comparative water absorbent resin (6) thus produced had a moisture content of 5.1 weight %. Other physical properties are shown in Table 1.

The aluminum sulfate aqueous solution was a mixture of a 27 weight % aluminum sulfate aqueous solution (8 weight % based on aluminum oxide), a 60 weight % sodium lactate aqueous solution, and 1,2-propylene glycol at a mixing ratio (weight ratio) of 1.0:0.3:0.025. The aluminum sulfate aqueous solution was added in an amount of 2.5 parts by weight based on 100 parts by weight of the comparative water absorbent resin (1).

The above drying was carried out in a windless state at 60° C. for 1 hour. The above sizing involved use of a JIS standard sieve having a mesh size of 850 μm.

Production Example 2

A sodium acrylate aqueous solution, an acrylic acid, ion-exchange water, and polyethylene glycol diacrylate (9 ethylene oxide units on average) as an internal crosslinking agent were put into a kneader-type reactor provided with two sigma blades. A monomer aqueous solution (b) was thus prepared. The monomer aqueous solution (b) had a monomer concentration of 38 weight % and a neutralization rate of 75 mol %. The internal crosslinking agent was used in an amount of 0.05 mol % based on the monomer.

Next, nitrogen gas was blown into the monomer aqueous solution (b) to reduce dissolved oxygen, and the entire atmosphere in the reactor was also replaced with nitrogen. Then, while the two sigma blades were rotated, sodium persulfate and L-ascorbic acid were added as polymerization initiators so that their respective amounts would be 0.05 mol % and 0.0003 mol %. After the addition, stirring polymerization started in the kneader-type reactor. Approximately 40 minutes after the start, particulate hydrogel-like crosslinked polymer (b) having an average particle size of approximately 2 mm was produced.

The particulate hydrogel-like crosslinked polymer (b) produced through the above operation was then spread thinly on a porous plate of a band dryer, and was dried with hot-air at 180° C. for 40 minutes, to thereby produce block-shaped dried polymer (b). Next, the dried polymer (b) was continuously supplied into a roll mill and pulverized therein, and was then continuously classified with use of a classification apparatus provided with JIS standard sieves having respective mesh sizes of 710 μm and 150 μm.

The above series of operations produced water absorbent resin powder (B) made up of particles (i) each with a diameter of not less than 150 μm and less than 710 μm and (ii) having a content of not less than 90 weight %. The water absorbent resin powder (B) thus produced had a weight average particle diameter (D50) of 350 μm, a water absorption capacity without load (CRC) of 44 (g/g), and a moisture content of 4.0 weight %.

Example 7

An operation identical to that of Example 1 above was conducted except that the water absorbent resin powder (A) was replaced with the water absorbent resin powder (B) produced in Production Example 2, to thereby produce water absorbent resin (7). The water absorbent resin (7) thus produced had a moisture content of 7.5 weight %. Other physical properties are shown in Table 1.

The surface-crosslinking treatment involved a heat treatment time of 42 minutes. Water absorbent resin particles (7) immediately after being discharged from the paddle dryer had a temperature of 101° C.

Example 8

An operation identical to that of Example 2 above was conducted except that the water absorbent resin powder (A) was replaced with the water absorbent resin powder (B) produced in Production Example 2, to thereby produce water absorbent resin (8). The water absorbent resin (8) thus produced had a moisture content of 6.3 weight %. Other physical properties are shown in Table 1.

The surface-crosslinking treatment involved a heat treatment time of 42 minutes. Water absorbent resin particles (8) immediately after being discharged from the paddle dryer had a temperature of 101° C.

Comparative Example 7

An operation identical to that of Comparative Example 1 above was conducted except that the water absorbent resin powder (A) was replaced with the water absorbent resin powder (B) produced in Production Example 2, to thereby produce comparative water absorbent resin (7). The comparative water absorbent resin (7) thus produced had a moisture content of 4.3 weight %. Other physical properties are shown in Table 1.

The surface-crosslinking treatment involved a heat treatment time of 42 minutes. Comparative water absorbent resin particles (7) immediately after being discharged from the paddle dryer had a temperature of 100° C.

Example 9

The water absorbent resin powder (B) produced in Production Example 2 above was continuously supplied to a high-speed stirring-type mixing apparatus (Turbulizer, available from Hosokawa Micron Corporation) in a processing amount of 70 (kg/hr). Next, a surface-crosslinking agent solution (9) prepared in advance was added to the mixing apparatus and mixed therein, to produce a dampened mixture (9). The surface-crosslinking agent solution (9) was a mixture of 0.02 part by weight of ethylene glycol diglycidyl ether, 2.0 parts by weight of isopropyl alcohol, and 4.0 parts by weight of ion-exchange water based on 100 parts by weight of the water absorbent resin powder (B).

The mixture (9) produced through the above operation was continuously supplied to a paddle-type indirect heating reactor (paddle dryer, available from Nara Machinery Co., Ltd.) adjusted to have a temperature of the atmosphere of 125° C. and a dew point of the atmosphere of 90° C. (relative humidity of 30% RH) for a surface-crosslinking reaction. The paddle dryer had (i) an inner wall surface (paddle and jacket) heated with use of a heat medium having a temperature of 125° C. and (ii) a top plate having a temperature retained with use of vapor of 0.2 MPa (approximately 120° C.). The surface-crosslinking reaction involved a heat treatment time of 30 minutes. Water absorbent resin particles (9) immediately after being discharged from the paddle dryer had a temperature of 105° C.

Next, the water absorbent resin particles (9) discharged from the paddle dryer were passed through a JIS standard sieve having a mesh size of 850 μm and were sized, to produce water absorbent resin (9). The water absorbent resin (9) thus produced had a moisture content of 8.5 weight %. Other physical properties are shown in Table 1.

Example 10

An operation similar to that of Example 9 above was conducted except that the temperature of the atmosphere in the paddle dryer was adjusted to 105° C., that the dew point of the atmosphere in the paddle dryer was adjusted to 75° C. (relative humidity of 32% RH), and that the temperature of the heat medium was adjusted to 110° C., to thereby produce water absorbent resin (10). The water absorbent resin (10) thus produced had a moisture content of 7.9 weight %. Other physical properties are shown in Table 1.

The water absorbent resin particles (10) immediately after being discharged from the paddle dryer had a temperature of 95° C.

Comparative Example 8

An operation similar to that of Example 9 above was conducted except that the temperature of the atmosphere in the paddle dryer was adjusted to 70° C. and that the dew point of the atmosphere in the paddle dryer was adjusted to 45° C. (relative humidity of 31% RH), to thereby produce comparative water absorbent resin (8). The comparative water absorbent resin (8) thus produced had a moisture content of 5.0 weight %. Other physical properties are shown in Table 1.

The comparative water absorbent resin particles (8) immediately after being discharged from the paddle dryer had a temperature of 95° C.

Comparative Example 9

An experiment was conducted in conformity to Example 1 of Japanese Examined Patent Publication (Kokoku) No. 6-55838 (1994) (hereinafter referred to as "Official Publication 1"). The powder D used in Example 1 of Official Publication 1 was replaced with the water absorbent resin powder (B) produced in Production Example 2 of the present application.

Specifically, the water absorbent resin powder (B) was continuously supplied in a processing amount of 35 (kg/hr) to the mixing apparatus disclosed in Example 1 of Official Publication 1. Next, a comparative surface-crosslinking agent solution (9) prepared in advance was added to the mixing apparatus and mixed therein, to produce a dampened comparative mixture (9). The comparative surface-crosslinking agent solution (9) was a mixture of 0.1 part by weight of ethylene glycol diglycidyl ether and 1 part by weight of methanol based on 100 parts by weight of the water absorbent resin powder (B).

The comparative mixture (9) produced through the above operation was continuously supplied to a paddle dryer adjusted to have a temperature of the atmosphere of 80° C. and a dew point of the atmosphere of 65° C. (relative humidity of 53% RH) for a surface-crosslinking treatment. The paddle dryer had (i) an inner wall surface (paddle and jacket) heated with use of a heat medium having a temperature of 85° C. and (ii) a top plate having a temperature not retained. The surface-crosslinking treatment involved a heat treatment time of 60 minutes. Comparative water absorbent resin particles (9) immediately after being discharged from the paddle dryer had a temperature of 80° C.

Next, the comparative water absorbent resin particles (9) discharged from the paddle dryer were passed through a JIS standard sieve having a mesh size of 850 μm and were sized, to produce comparative water absorbent resin (9). The comparative water absorbent resin (9) contained a large number of agglomerates each having a diameter of approximately 2 mm, and the number of such agglomerates tended to increase as the operating time passed.

When 6 hours passed after the start of the production, the operation was stopped as the amount of the comparative water absorbent resin (9) passing through the JIS standard sieve decreased. Then, the inside of the paddle dryer was inspected, with the result of water absorbent resin being found to be adhering to the top plate.

The comparative water absorbent resin (9) produced by the time the operation was stopped had a moisture content of 8.0 weight %. Other physical properties are shown in Table 1.

a high relative humidity. This practice unfortunately causes trouble due to condensation as indicated by the results of Comparative Example 9, and has failed to improve productivity. However, the results of Examples 1, 3, 9, and 10 show

TABLE 1

|  | Water absorbent resin powder | Heat treatment (surface-crosslinking reaction) | | | | | Temperature of water absorbent resin particles (powder temperature) [° C.] | Water absorbent resin | | | |
|---|---|---|---|---|---|---|---|---|---|---|---|
|  |  | Temperature of atmosphere [° C.] | Dew point of atmosphere [° C.] | Relative humidity of atmosphere [% RH] | Heat treatment time [min] | Powder relative humidity [%] |  | Moisture content [%] | CRC [g/g] | AAP [g/g] | Dusting rate [%] |
| Example 1 | (A) | 130 | 80 | 18 | 42 | 45 | 101 | 7.9 | 42 | 31 | 0.8 |
| Example 2 | (A) | 109 | 65 | 18 | 42 | 24 | 101 | 6.8 | 42 | 30 | 1.1 |
| Comparative Example 1 | (A) | 83 | 45 | 18 | 42 | 9 | 100 | 4.9 | 42 | 26 | 2.2 |
| Comparative Example 2 | (A) | 130 | 80 | 18 | 42 | 3 | 195 | 1.2 | 36 | 27 | 4.1 |
| Example 3 | (A) | 145 | 95 | 20 | 21 | 44 | 119 | 8.5 | 38 | 33 | 0.6 |
| Comparative Example 3 | (A) | 80 | 55 | 33 | 21 | 8 | 118 | 4.7 | 38 | 28 | 2.2 |
| Example 4 | (A) | 135 | 85 | 18 | 53 | 39 | 111 | 7.5 | 39 | 30 | 0.8 |
| Comparative Example 4 | (A) | 135 | 35 | 2 | 53 | 4 | 110 | 2.8 | 39 | 25 | 3.2 |
| Example 5 | (A) | 130 | 80 | 18 | 42 | 45 | 101 | 7.9 | 42 | 22 | 0.9 |
| Comparative Example 5 | (A) | 83 | 45 | 18 | 42 | 9 | 100 | 4.9 | 42 | 16 | 2.3 |
| Example 6 | (A) | 130 | 80 | 18 | 42 | 45 | 101 | 8.0 | 41 | 28 | 0.8 |
| Comparative Example 6 | (A) | 83 | 45 | 18 | 42 | 9 | 100 | 5.1 | 41 | 22 | 2.2 |
| Example 7 | (B) | 130 | 80 | 18 | 42 | 45 | 101 | 7.5 | 36 | 34 | 0.9 |
| Example 8 | (B) | 109 | 65 | 18 | 42 | 24 | 101 | 6.3 | 36 | 32 | 1.3 |
| Comparative Example 7 | (B) | 83 | 45 | 18 | 42 | 9 | 100 | 4.3 | 36 | 29 | 2.4 |
| Example 9 | (B) | 125 | 90 | 30 | 30 | 58 | 105 | 8.5 | 34 | 34 | 0.7 |
| Example 10 | (B) | 105 | 75 | 32 | 30 | 46 | 95 | 7.9 | 35 | 33 | 0.8 |
| Comparative Example 8 | (B) | 70 | 45 | 31 | 30 | 11 | 95 | 5.0 | 35 | 28 | 2.1 |
| Comparative Example 9 | (B) | 80 | 65 | 53 | 60 | 53 | 80 | 8.0 | 39 | 19 | 1.1 |

CONCLUSION

Comparisons between Examples 1 and 2 and Comparative Example 1, between Example 3 and Comparative Example 3, between Example 4 and Comparative Example 4, between Examples 7 and 8 and Comparative Example 7, and between Examples 9 and 10 and Comparative Example 8 show that in a case where a heat treatment is carried out in a state where the dew point of the atmosphere in the reactor is not lower than 60° C., water absorbent resin to be produced will have an improved water absorption capacity under load (AAP). This tendency remains the same even after the addition of an additive (according to a comparison between Examples 5 and 6 and Comparative Examples 5 and 6).

The comparisons also show that in a case where (i) the dew point of the atmosphere in the reactor is not lower than 60° C., and (ii) water absorbent resin particles have a temperature (powder temperature) of not higher than 130° C., water absorbent resin to be produced will have a high moisture content and a low dusting rate (excellent impact resistance). Further, the comparisons indicate that the moisture content of water absorbent resin is highly correlated not with the atmospheric relative humidity but with the powder relative humidity and that the powder relative humidity should be controlled so that it is not less than 15%.

To produce water absorbent resin having a high moisture content, conventional practice has been such that a surface-crosslinking reaction is carried out in an atmosphere having that in a case where (i) water absorbent resin particles have a temperature (powder temperature) of not lower than 90° C., and (ii) the reactor has an inner wall surface with a temperature controlled so that the temperature is not lower than 100° C., it is possible to stably produce water absorbent resin having a moisture content higher than conventional.

INDUSTRIAL APPLICABILITY

The method of the present invention for producing a polyacrylic acid (salt)-based water absorbent resin is applicable to production, in particular mass production, of water absorbent resin. The polyacrylic acid (salt)-based water absorbent resin produced through the method of the present invention is suitably used as an absorbent body for a sanitary product such as a disposable diaper.

The invention claimed is:

1. A method for producing a polyacrylic acid (salt)-based water absorbent resin,
the method comprising a surface-crosslinking step,
a surface-crosslinking agent being added in a form of an aqueous solution to a water absorbent resin powder, and the aqueous solution has a water content of 1 part by weight to 15 parts by weight based on 100 parts by weight of the water absorbent resin powder,
the water absorbent resin powder containing particles each having a diameter of less than 150 μm at a proportion of 0 weight % to 10 weight %, the surface-crosslinking step including a reaction step, the reaction step involving using a reactor having (i) an inner wall surface having a temperature within a range of 100° C. to 250° C. and (ii) an inside atmosphere having a dew point within a range of 65° C. to 95° C., the reaction step including heat-treating a water absorbent resin mixture to control a powder temperature so that the powder temperature is 90° C. to 130° C., wherein the powder temperature is a maximum temperature during the reaction step.

2. The method according to claim 1, wherein the inside atmosphere has a temperature within a range of 100° C. to 150° C.

3. The method according to claim 1, wherein a powder relative humidity during the reaction step is from 15% to 100%.

4. The method according to claim 1, wherein the heat treatment during the reaction step is carried out for 5 minutes to 60 minutes.

5. The method according to claim 1, wherein the surface-crosslinking step involves using, as a surface-crosslinking agent, at least one compound selected from the group consisting of an epoxy compound, a haloepoxy compound, and an oxetane compound.

6. The method according to claim 1, wherein the polyacrylic acid (salt)-based water absorbent resin produced through the surface-crosslinking step has a moisture content within a range of 6 weight % to 15 weight %.

7. The method according to claim 1, wherein the water absorbent resin powder has a weight average particle diameter (D50) of 250 μm to 500 μm;

the water absorbent resin powder contains particles each having a diameter of less than 150 μm at a proportion of 0 weight % to 5 weight %; and the water absorbent resin powder contains particles each having a diameter of not less than 850 μm at a proportion of 0 weight % to 5 weight %.

8. The method according to claim 1, wherein the surface-crosslinking agent is added to the water absorbent resin powder having a temperature of 30° C. to 100° C.

9. The method according to claim 1, wherein the reactor is a paddle reactor.

10. The method according to claim 1, wherein the reactor is a continuous reactor having an inclination of more than 0° and not more than 20° downward relative to the horizontal plane.

11. The method according to claim 1, wherein the surface-crosslinking agent in the form of the aqueous solution is sprayed or dropped onto the water absorbent resin powder to be mixed therewith in a high-speed stirring continuous mixing apparatus.

12. The method according to claim 1, wherein the polyacrylic acid (salt)-based water absorbent resin which has been surface-crosslinked has a water absorption capacity under load (AAP under load of 0.3 psi) of not less than 20 (g/g).

13. The method according to claim 1, wherein, in the reaction step in the surface-crosslinking step, a gas is introduced to the reactor that is used, wherein the gas is selected from the group consisting of an inert gas, a mixture of the inert gas and water vapor, and steam; wherein the inert gas is selected from the group consisting of air, dry air, nitrogen, helium, and argon.

14. The method according to claim 1, wherein, in the reaction step in the surface-crosslinking step, a pressure inside the reactor that is used is different from the atmospheric pressure by −10 kPa to 0 kPa.

* * * * *